United States Patent [19]

Nappholz et al.

[11] 4,429,697
[45] Feb. 7, 1984

[54] DUAL CHAMBER HEART PACER WITH IMPROVED VENTRICULAR RATE CONTROL

[75] Inventors: Tibor A. Nappholz, Drummoyne; Ronald C. Bradbury, Marsfield; Bruce R. Satchwell, Pymble, all of Australia

[73] Assignee: Telectronics Pty. Ltd., Lane Cove, Australia

[21] Appl. No.: 367,427

[22] Filed: Apr. 12, 1982

[51] Int. Cl.³ .............................................. A61N 1/36
[52] U.S. Cl. ............................................. 128/419 PG
[58] Field of Search ...................... 128/419 PG, 419 P

[56] References Cited

U.S. PATENT DOCUMENTS

| | | | |
|---|---|---|---|
| 3,768,486 | 10/1973 | Berkovits | 128/419 PG |
| 3,857,399 | 12/1974 | Zacouto | 128/419 PG |
| 3,903,897 | 9/1975 | Woolons et al. | 128/419 PG |
| 4,059,116 | 11/1977 | Adams | 128/419 PG |
| 4,091,817 | 5/1978 | Thaler | 128/419 PG |

Primary Examiner—William E. Kamm
Attorney, Agent, or Firm—Gottlieb, Rackman & Reisman

[57] ABSTRACT

A dual-chamber heart pacer whose ventricular pacing rate is closely matched to the physiological requirements of the patient. A "true" atrial rate is determined by counting over a 3-second interval the number of sensed atrial beats, including those which occur during atrial refractory periods. When the atrial rate rises to a threshold level, the ventricular pacing rate decreases gradually from the Wenckebach rate to a fall-back rate independent of atrial sensing. During this decline, atrial pacing pulses may be generated simultaneously with ventricular pacing pulses in an effort to terminate tachycardia. The controlled decline in ventricular pacing rate begins after a 3:2 block has resulted, but before a 2:1 block would otherwise result. The fall-back rate is higher than the standby rate to compensate for the lack of atrial pacing when the system operates at the fall-back rate.

119 Claims, 9 Drawing Figures

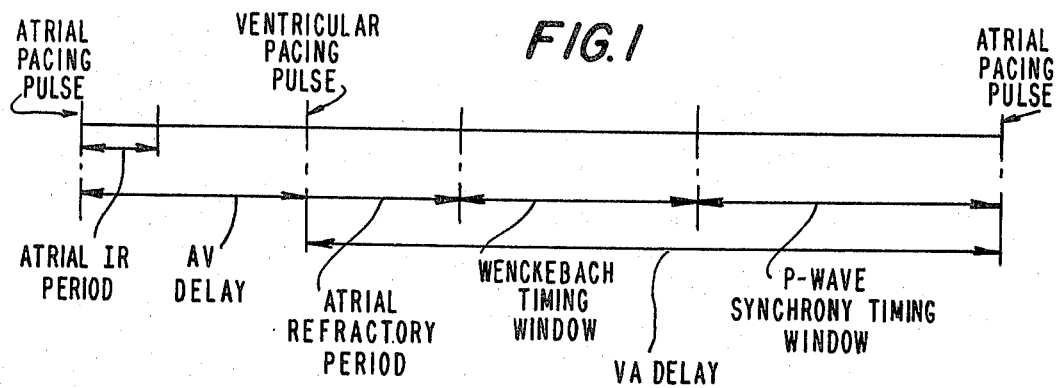

FIG. 1

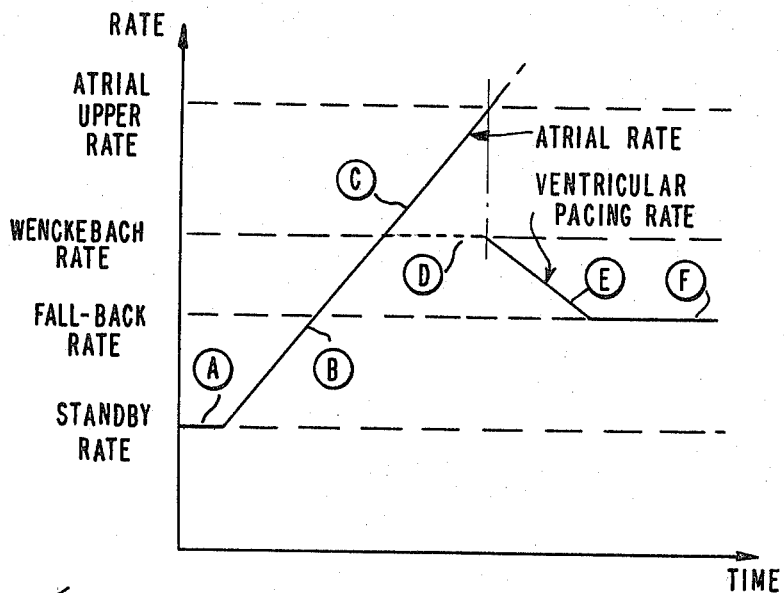

FIG. 2

A = VENTRICULAR SENSE DISABLE WHEN AUR = 0
B = ATRIAL SENSE ENABLE
C = INHIBIT OR SYNCHRONOUS PACING WHEN AUR = 0
D = ATRIAL PACING WHEN AUR = 0
E = ATRIAL PACING WHEN AUR = 1, ABOVE FALL-BACK RATE
F = VENTRICULAR PACING WHEN AUR = 1, ABOVE FALL-BACK RATE
G = INHIBIT OR SYNCHRONOUS PACING WHEN AUR = 1, ABOVE FALL-BACK RATE
H = VENTRICULAR SENSE DISABLE WHEN AUR = 1, ABOVE FALL-BACK RATE $$\text{VENTRICULAR SENSE DISABLE} = (\overline{FBR}) \cdot ((A \cdot \overline{AUR}) + (H \cdot AUR))$$

$$\text{ATRIAL PACE ENABLE} = (\overline{FBR}) \cdot ((D \cdot \overline{AUR}) + (E \cdot AUR))$$

$$\text{VENTRICULAR PACE DISABLE} = (\overline{FBR}) \cdot (F) \cdot (AUR) +$$
$$(R\ DETECT) \cdot ((C \cdot \overline{AUR}) + (G \cdot AUR) + (FBR))$$

FIG. 7

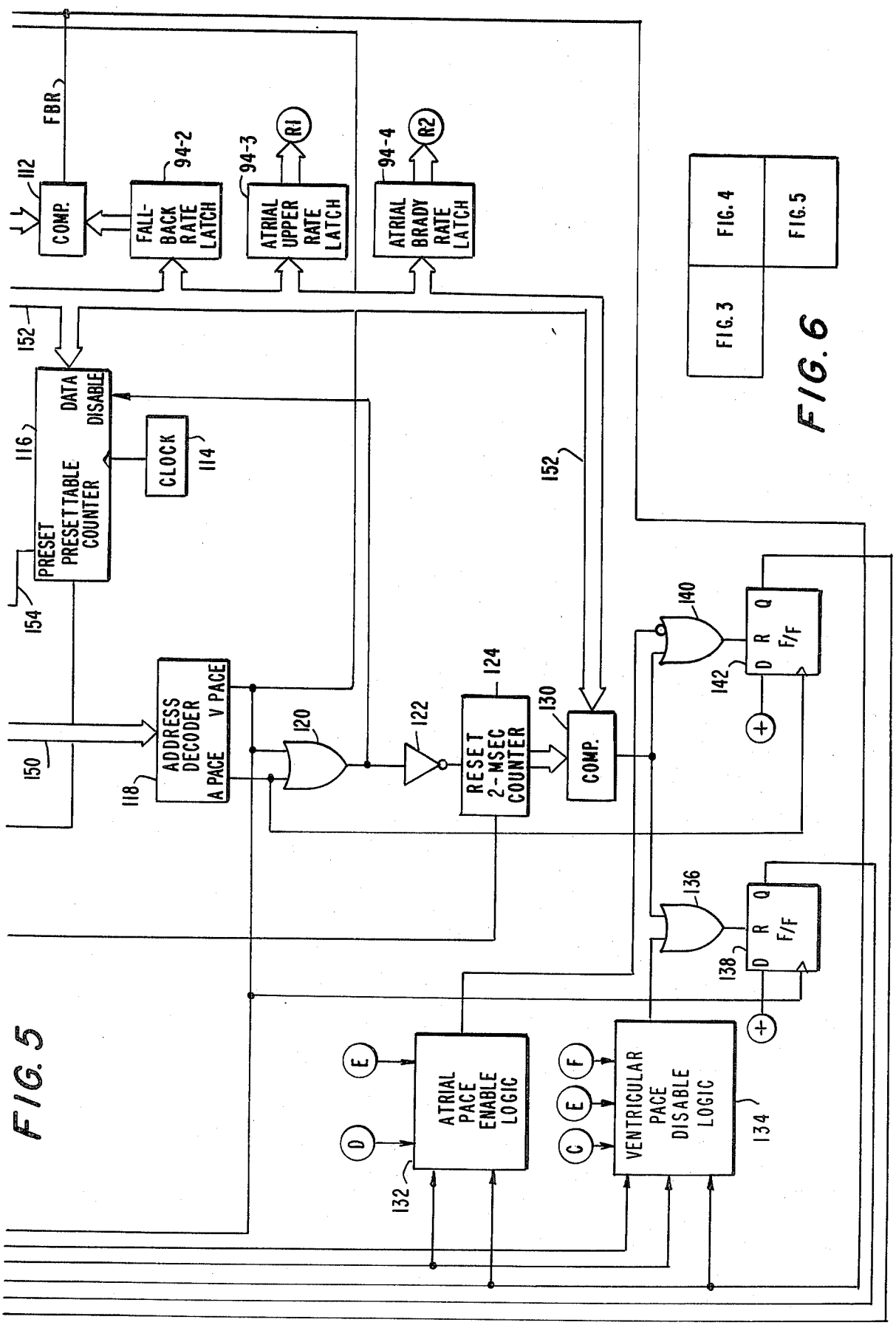

DUAL CHAMBER HEART PACER WITH IMPROVED VENTRICULAR RATE CONTROL

DESCRIPTION

This invention relates to heart pacers, and more particularly to a dual chamber heart pacer which generates ventricular pacing pulses at rates which closely match the physiological requirements of the patient.

A conventional dual chamber heart pacer is provided with atrial beat sensing and pulse generating circuits, and ventricular beat sensing and pulse generating circuits. The detection of a ventricular beat, or the generation of a ventricular pacing pulse, initiates the timing of an interval known as the VA delay. If an atrial beat is not sensed prior to expiration of the VA delay interval, then an atrial pacing pulse is generated. Following the generation of an atrial pacing pulse, or following the sensing of an atrial beat (in which case an atrial pacing pulse is not generated), an interval known as the AV delay is timed. If a ventricular beat is not sensed prior to expiration of this timing interval, then a ventricular pacing pulse is generated. With the generation of a ventricular pacing pulse, or the sensing of a ventricular beat, the VA delay timing begins once again.

Although the basic timing of a dual chamber pacer is that just described, there are numerous refinements which have been found to be advantageous. For example, the VA delay timing interval may be divided into three parts—the atrial refractory period, the Wenckebach timing window, and the P-wave synchrony timing window. Any atrial beats which are sensed during the atrial refractory period are ignored for purposes of synchronizng ventricular output to atrial activity. If an atrial beat is sensed during the Wenckebach timing window, the AV delay timing does not begin immediately; instead, it is only at the expiration of the Wenckebach timing that AV delay timing begins. The sensing of an atrial beat at any time during the P-wave synchrony timing window results in immediate triggering of the AV delay timing.

Atrial beats which are sensed during the atrial refractory period are ignored because otherwise heart pacing might occur at a dangerously high rate. It is only when an atrial beat is sensed during the P-wave synchrony timing window that it is assumed that the atria and ventricles are beating in synchronism, so that AV delay timing can begin immediately. Atrial beats which are sensed during the Wenckebach timing window are indicative of an atrial rate which is too fast, but a rate which is still low enough for an attempt to be made to synchronize ventricular pacing to atrial beats. By postponing the start of he AV delay timing until the end of the Wenckebach timing window, in effect the AV delay interval is lengthened and the "beat-to-beat" or "instantaneous" ventricular pacing rate is maintained at the Wenckebach rate. During successive cycles of operating, an atrial beat is sensed earlier and earlier during the Wenckebach timing window. Eventually, an atrial beat is sensed during the atrial refractory period, in which case a corresponding ventricular pacing pulse is not generated at all. The net effect is that a sort of guasi-synchronism is maintained between the sensing of atrial beats and the generation of ventricular pacing pulses, although for each N atrial beats only (N-1) ventricular pacing pulses are generated. This is known as an N:(N−1) "block", with N decreasing as the rate of atrial beats increases. The "blocking" phenomenon commences at an atrial rate which is known as the "Wenckebach" rate.

If the atrial rate is too high, however, it makes little sense to even attempt to maintain synchronism between sensed atrial beats and ventricular pacing pulses; synchronism is hardly desirable because pacing the ventricles at such a high rate could be dangerous and so many pacing pulses would be skipped as a result of the Wenckebach phenomenon that even quasi-synchronism would be meamningless. While prior art pacers of both single-chamber and dual-chamber types have generally provided a mechanism for limiting the ventricular pacing rate to a maximum safe value, they have generally not controlled the ventricular pacing rate to match the physiological requirements of the patient.

It is a general object of our invention to provide a heart pacer in which the ventricular pacing rate more closely matches the physiological requirements of the patient when the atrial rate rises above a predetermined threshold value.

It is not enough, however, simply to call for improved ventricular pacing rate control following the atrial rate rising to a threshold value. The problem is that there is no effective way to even measure the "atrial rate" when the many atrial beats which are sensed during atrial refractory periods are ignored. The atria may be beating too fast, but they are still beating. Ignoring a significant percentage of the beats can only give rise to an inaccurate indication of the atrial rate.

It is therefore another object of our invention to provide a mechanism which allows a more accurate determination of the atrial rate to be made.

In accordance with the principles of our invention, the average atrial rate is determined, for example, by counting the number of atrial beats which are sensed during an interval long enough to permit an average rate value to be determined (three seconds in the illustrative embodiment of the invention). All atrial beats which are sensed are counted, even those which occur during the atrial refractory period and those which occur during the AV delay interval (provided that they do not occur during an atrial interference reversion period, as will be described below), and which are otherwise ignored insofar as initiating the AV delay timing is concerned. (U.S. Pat. No. 4,298,007, issued on Nov. 3, 1981 and entitled "Atrial Rate Sensitive Cardiac Pacer Circuit", discloses a similar averaging technique but one which ignores atrial beats which occur before the end of the atrial refractory period.) The exception to this general rule is that any atrial beat which is sensed within a short interval (30 milliseconds in the illustrative embodiment of the invention) preceding a subsequently sensed ventricular beat is not counted; due to the relatively high sensitivity of the atrial sense amplifier, it is assumed that the sensing of an atrial beat which is shortly followed by the sensing of a ventricular beat did not result from an actual atrial beat, but rather resulted from the atrial sense amplifier having detected the ventricular beat even before the ventricular sense amplifier detected it.

At lower atrial rates, the best possible synchronism is maintained; for every atrial beat which is sensed, a ventricular pacing pulse is generated if one is needed. When the atrial rate exceeds the Wenckebach rate, the blocking phenomenon begins with atrial beats being sensed during the Wenckebach timing window earlier and earlier in successive cycles until eventually an atrial beat occurs during the atrial refractory period and results in a skipped ventricular pacing pulse. Once the atrial rate rises to a predetermined upper limit referred to as the atrial upper rate, however, the system no longer even tries to maintain synchronism.

Instead, the system operates in the VVI mode. Ventricular pacing pulses are generated on demand, and the V-V timing interval is the reciprocal of a programmable "fall-back" rate. Because there is no atrial pacing at this time and the overall pacing is therefore not as efficient as it should be, the fall-back rate is made higher than the "standby" rate, the latter being the minimum ventricular pacing rate (the reciprocal of the sum of the AV and VA delays).

Prior to the atrial rate exceeding the atrial upper rate, the ventricular pacing rate equals the Wenckebach rate except for the occasional pacing pulse which is skipped. A ventricular pacing pulse is generated during most cycles, it being understood that every now and then a pacing pulse is skipped depending upon the degree of the block. What is of importance is the manner in which the ventricular pacing rate is caused to switch between the Wenckebach rate and the lower-value fall-back rate, as well as when the transition begins.

As the atrial rate increases, the degree of the block becomes more pronounced, following a sequence such as 5:4, 4:3, 3:2, etc. A change from a 3:2 block to a 2:1 block is the most pronounced because it is at this time that the greatest percentage change occurs in the average number of ventricular pacing pulses which are generated. Since the atrial rate is very high, it is an indication that the patient's heart is beating rapidly and his blood vessels are dilated. A sudden drop in the average number of ventricular pacing pulses which are generated can result in a significant decrease in blood pressure, and because the blood vessels are dilated at this time the patient may experience dizziness. For this reason, the atrial upper rate which is selected for controlling a transition in the ventricular pacing rate from the Wenckebach rate to the fall-back rate is such that the transition begins before a 2:1 block has taken place. Preferably, the transition begins after a 3:2 block has resulted. The system is programmed with an atrial upper rate which allows the controlled transition in the ventricular pacing rate to begin after the desired degree of block has resulted, depending upon the particular values of the intervals which control the overall timing.

When the atrial rate rises above the atrial upper rate, the ventricular pacing rate starts to decrease from the Wenckebach rate to the fall-back rate in a controlled manner, independent of atrial beat sensing. Typically, the transition requires 6–10 seconds. In the illustrative embodiment of the invention, the interval between successive ventricular pacing pulses increases by 20 milliseconds during successive cycles of operation. The gradual transition in the ventricular pacing rate is much more desirable than a sudden drop, and it more clearly matches the patient's physiological requirements. In the preferred embodiment of the invention, the controlled decline in ventricular pacing rate does not necessarily begin at the Wenckebach rate. As soon as the atrial rate exceeds the atrial upper rate, ventricular pacing begins at a rate known as the "back-up" rate. Although the backup rate is usually programmed to equal the Wenckebach rate, it may be different.

Once ventricular pacing pulses are being generated at the constant fall-back rate, they continue to be so generated until the atrial rate drops below the atrial upper rate. It is only when the atrial rate drops below the threshold limit that there is a sudden change in the mode of operation. Instead of continuing to pace at the fall-back rate (or at a varying rate in the transition region should the atrial rate decrease below the threshold level within a few seconds after it rises above it), the sensing of atrial beats once again affects the system timing with ventricular pacing pulses being generated at the Wenckebach rate, but with some ventricular pacing pulses being blocked.

A particular feature of interest is the programmable option of having an atrial pacing pulse generated approximately simultaneously with a ventricular pacing pulse during the transition from the Wenckebach rate to the fall-back rate following the atrial rate first exceeding the upper limit. The high atrial rate may be due to the patient experiencing tachycardia. Tachycardia may be terminated by pacing the heart at a fast rate, and it is sometimes even more efficacious to provide atrial pacing than ventricular pacing toward this end. For this reason, it may be desirable to generate atrial pacing pulses together with (or even without) ventricular pacing pulses as the pacing rate is reduced to the fall-back rate. In the illustrative embodiment of the invention, the same timing circuit is used to control the generation of both types of pacing pulses. For this reason atrial and ventricular pacing pulses cannot be generated simultaneously. However, they can be generated within two milliseconds of each other, and this approximately simultaneous dual chamber pacing is from a practical standpoint simultaneous. As mentioned above, the controlled reduction in ventricular pacing rate begins at a programmable back-up rate. Although the back-up rate is usually set to equal the Wenckebach rate so that the patient does not experience a sudden change in pacing rate, the back-up rate may be made higher than the Wenckebach rate so that the rapid pacing pulses have a better chance of terminating tachycardia.

Further objects, features and advantages of our invention will be understood upon consideration of the following detailed description in conjunction with the drawing, in which:

FIG. 1 depicts the basic timing mechanism employed in the illustrative embodiment of the invention;

FIG. 2 is a curve which depicts the ventricular pacing rate as a function of both atrial rate and time in the illustrative embodiment of the invention;

Figure 3:
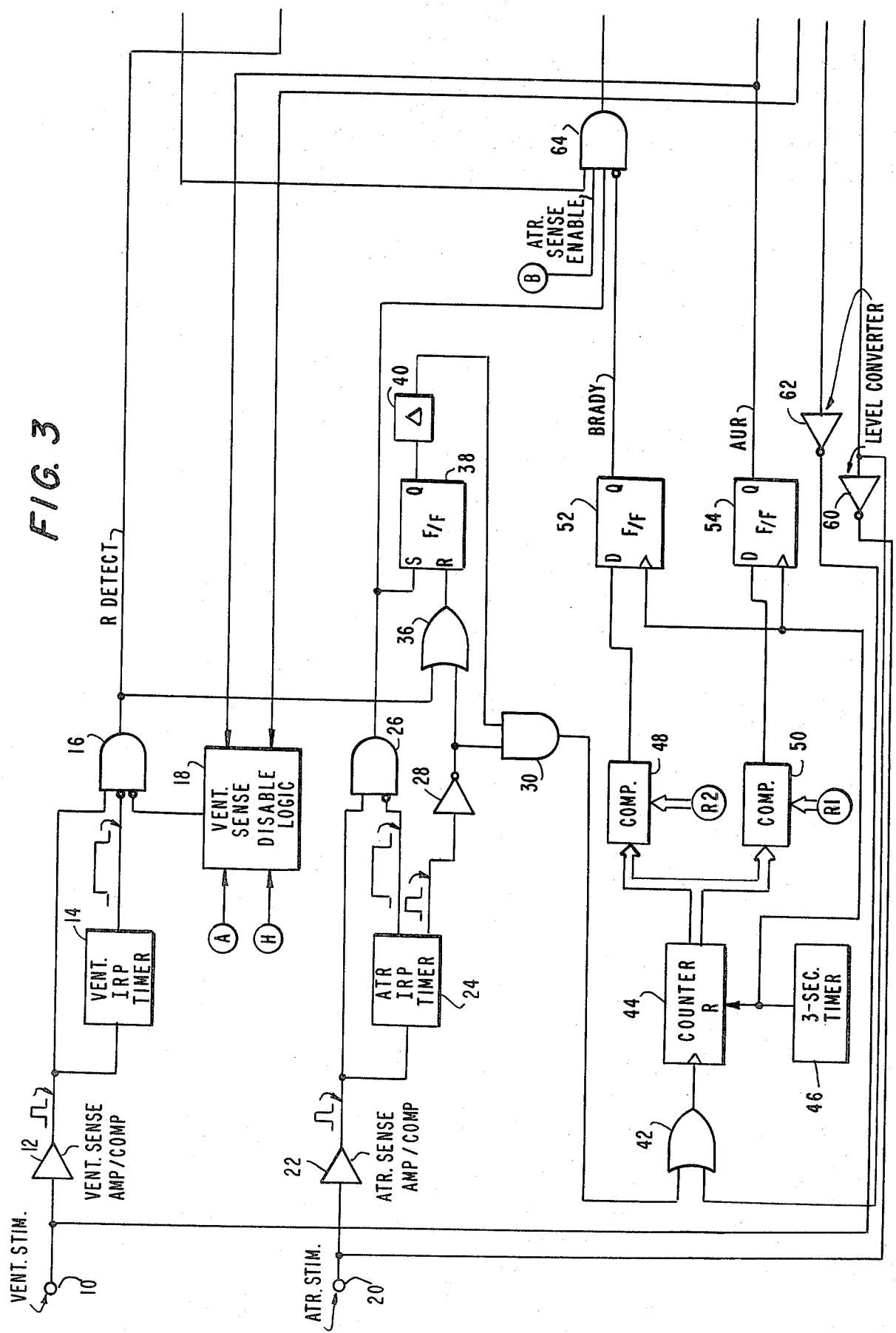
Figure 4:
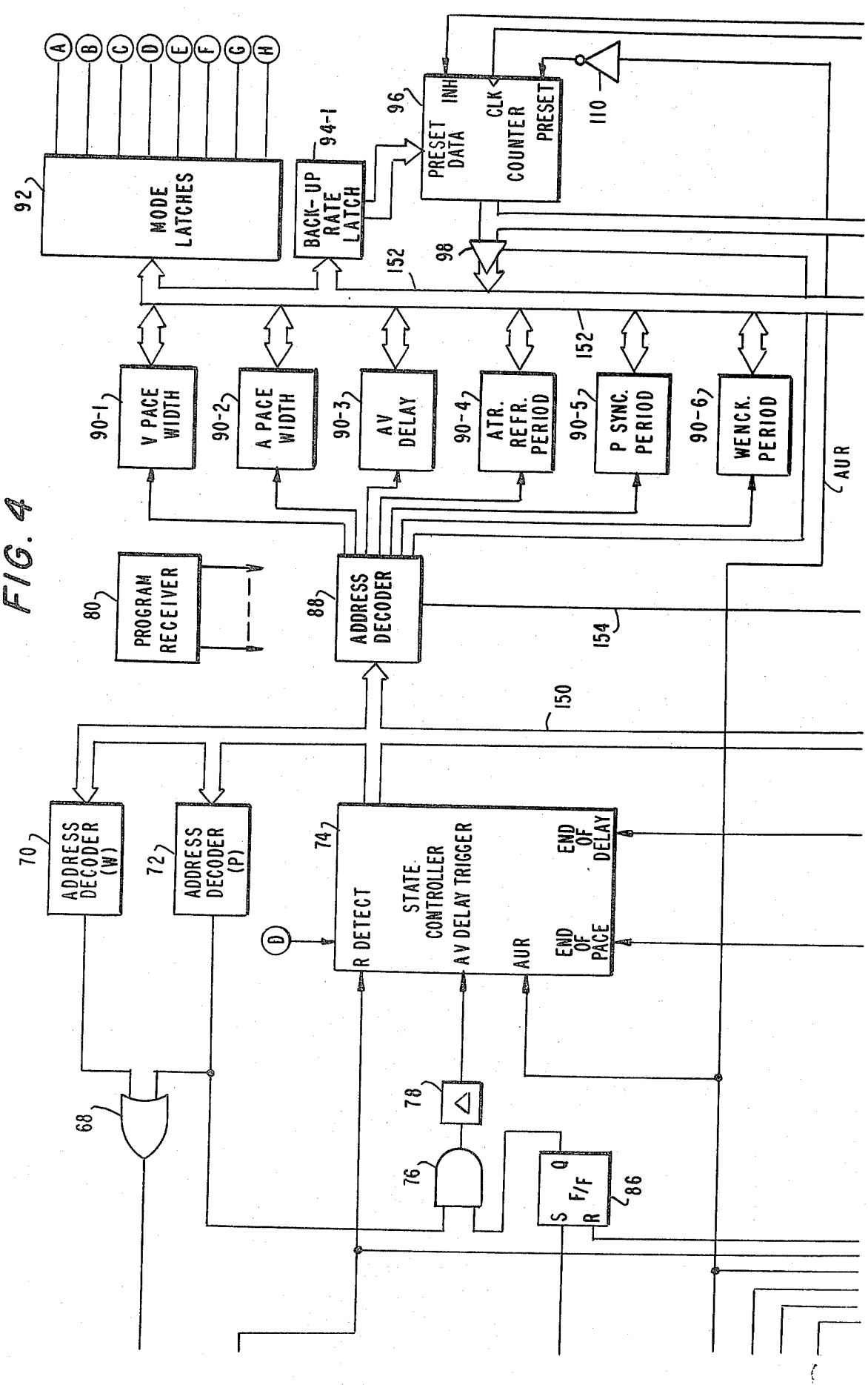
Figure 8:
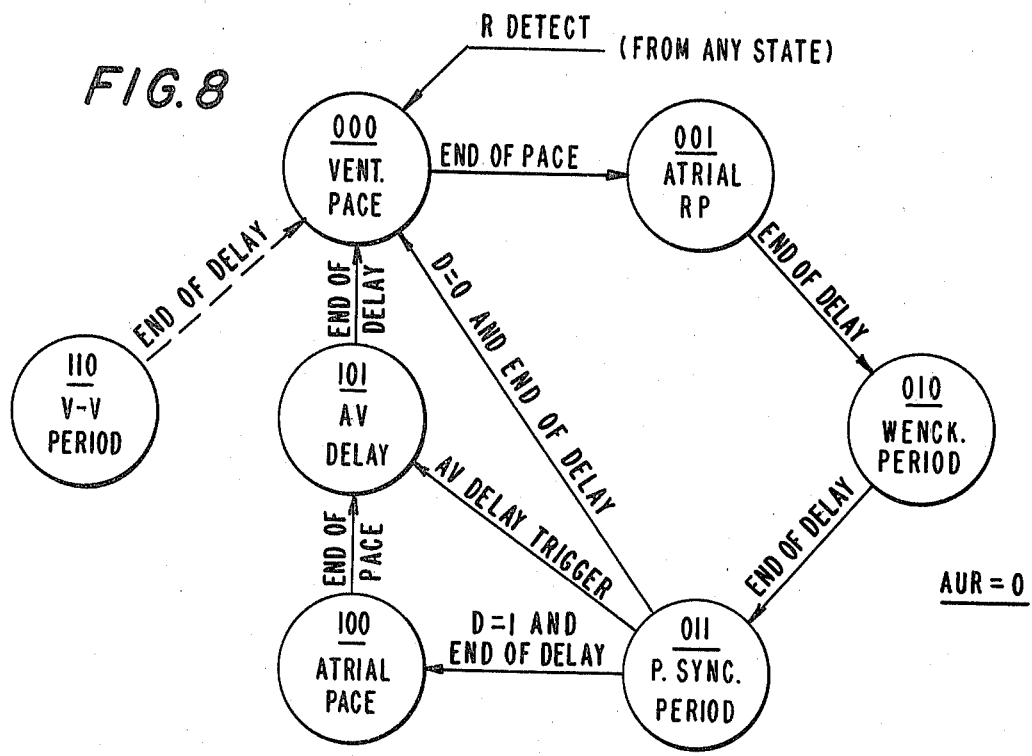
Figure 9:
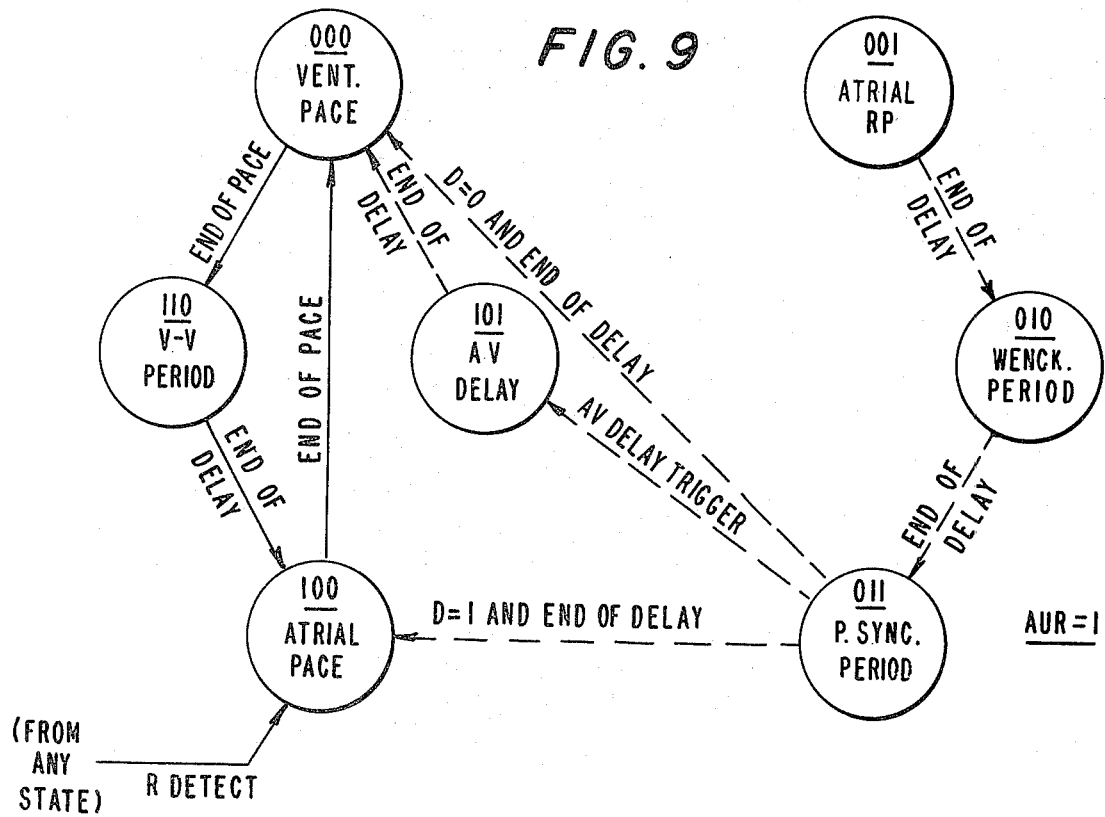

FIGS. 3–5, arranged as shown in FIG. 6, are a schematic of the illustrative embodiment of the invention;

FIG. 7 defines eight programmable mode bits which control the system operation, and also sets forth the Boolean equations which characterize three logic circuits;

FIG. 8 is a state diagram which characterizes the system operation when the atrial rate is below the atrial upper rate; and FIG. 9 is a state diagram which characterizes the system operation when the atrial rate is above the atrial upper rate.

In the following description it is to be understood that the only circuit details shown in FIGS. 3–5 are those which are necessary for an understanding of the present invention. For example, the pacer may be provided with a run-away protection circuit in the ventricular pacing pulse output stage, as is standard in the art; such a circuit is not shown in the drawing because it is not necessary for an understanding of the present invention. Similarly, the manner in which various latches can be programmed by the physician under external control is shown only symbolically; programming circuits are so standard in the art that the detailed illustration of such a scheme is hardly necessary. What is important is the information which is latched during a programming sequence, not which particular prior art program decoder is utilized.

Similarly, the instantaneous mode in which the system is operated is determined by a state controller. The state controller is shown as block 74 in FIG. 4, and it has several inputs and a 3-bit address output. The details of the state controller are not important for an understanding of the present invention. What are important are the individual states of the system (represented by respective 3-bit addresses) and the input signals which control transitions from one state to another. The state diagrams of FIGS. 8 and 9 completely define the operation of the state controller. The actual implementation of the state controller is straight-forward and the skills necessary to implement it are no different from those required in the design of any finite state machine. For example, three flip-flops can be provided to represent the seven states. The outputs of the flip-flops form the 3-bit address bus 150 in FIG. 4. Each flip-flop can be provided with a plurality of logic gates which, taking into consideration the current state represented by the flip-flops and the inputs to the state controller, generate the next state in sequence for the three flip-flops so that the required state is achieved on the next appropriate transition in a flip-flop clock signal.

Basic System Timing—FIG. 1

The basic system timing is depicted in FIG. 1. There are several sequential timing intervals between successive atrial pacing pulses (or atrial beats). Following any atrial beat, there is a fixed atrial interference reversion period, typically in the range 160-200 milliseconds. Another atrial beat which is detected during the interference reversion period is ignored; it is treated as noise and affects neither the basic system timing nor the atrial rate monitor which measures the average atrial rate over a three-second interval. Atrial beats which occur within 200 milliseconds of each other, for example, are equivalent to an instantaneous atrial rate of 300 beats per minute, a rate which is higher than any likely cardiac rate. If the atrial sense circuit detects activity at such a high rate, the sensed signals are assumed to have resulted from electromagnetic interference and the signals are ignored. All that happens when the atrial sense signal is detected within 160-200 milliseconds of a previous atrial sense signal is that the interference reversion period is triggered once again, so that another atrial sense signal which occurs within 160-200 milliseconds will also be ignored.

The AV delay timing is triggered by the sensing of an atrial beat or the generation of an atrial pacing pulse. If the ventricular beat is not detected within the AV delay period, a ventricular pacing pulse is generated at the end of the AV delay. With the generation of a ventricular pacing pulse or the sensing of a ventricular beat, the VA delay timing is triggered. If an atrial beat is not detected within the VA delay interval, then an atrial pacing pulse is generated at the end of the interval. With the generation of an atrial pacing pulse, or the detection of an atrial beat during the VA delay period, the AV delay timing is started once again.

The VA delay interval actually comprises three sequential intervals. The detection of an atrial beat during the atrial refractory period (following the detection of a ventricular beat or the generation of a ventricular pacing pulse) is ignored insofar as the basic system timing is concerned although it does increment the atrial rate monitor count. The atrial refractory period is provided to avoid sensing a retrograde conducted P wave following the generation of a ventricular pacing pulse, and to avoid atrial sensing of a ventricular ectopic beat which occurs during the ventricular refractory period. The atrial refractory period is a programmable parameter, and depending upon the patient's condition may be set between 0 and 600 milliseconds.

If an atrial beat is detected during the Wenckebach timing window, the AV delay timing does not begin immediately. Instead, the system registers the fact that an atrial beat was detected, but uses the information only at the end of the Wenckebach timing interval. It is only then that the AV delay timing commences. In effect, the AV delay is prolonged by the time between the detection of an atrial beat and the end of the Wenckebach timing interval. The purpose of the Wenckebach timing mechanism is to place an upper limit on the instantaneous ventricular pacing rate. The "Wenckebach rate" is the sum of the atrial refractory, Wenckebach and the AV-delay periods, expressed in beats per minute. As mentioned above, the atrial refractory period is programmable in the range of 0-600 milliseconds. The AV delay is programmable in the range of 0-315 milliseconds, and the Wenckebach timing window is programmable in the range of 0-1275 milliseconds.

If an atrial beat is detected during the P-wave synchrony timing window, then the AV delay timing begins immediately. Any atrial beat which occurs toward the end of the VA delay interval is sufficiently delayed after a ventricular beat to call for an immediate start of the AV delay timing. The P-wave synchrony timing window is also a programmable parameter, the window having a range of 0-2555 milliseconds.

The timing diagram of FIG. 1 does not depict the widths of the atrial and ventricular pacing pulses. As is standard in the art, these two parameters are also programmable, with each pulse varying between 0.125 and 1.625 milliseconds.

Although not shown in FIG. 1, there is also a ventricular interference reversion period whose timing is triggered by the detection of a ventricular beat or the generation of a ventricular pacing pulse. Another ventricular beat which is detected during this interference reversion period is ignored and has no effect other than to re-start the ventricular interference reversion timing once again. In the detailed circuit to be described below, the ventricular interference reversion period is not shown as being a programmable parameter so as not to unduly complicate the drawing. In actual practice, however, the period may be programmable within a range of 200-440 milliseconds.

Because in a typical dual-chamber pacer the atrial sense amplifier has a higher gain than the ventricular sense amplifier, there is a potential problem of a ventricular beat actually being sensed by the atrial amplifier before it is sensed by the ventricular amplifier. In the system of FIGS. 3-5 atrial beats are counted during three-second intervals in order to determine the atrial rate, and it would otherwise be possible for a ventricular beat to erroneously result in incrementing of the atrial beat counter if the atrial sense amplifier responds to a ventricular beat. For this reason, as will become apparent below, a delay of 30 milliseconds is inserted between the sensing of a beat by the atrial sense amplifier and the incrementing of the atrial beat counter. If during this 30-millisecond delay the ventricular sense amplifier detects a ventricular beat, then the atrial sense signal is cancelled and the atrial beat counter is not incremented. Although the initial sensing of the beat by the atrial sense amplifier does result in triggering of the AV delay timing, this is of no moment because as soon as the ventricular beat is detected by the ventricular sense amplifier the system switches to start VA delay timing.

There are additional nuances to the system timing, and they will be discussed below in connection with a description of the schematic of FIGS. 3-5. It is also to be appreciated that an actual pacer may have many more programmable parameters and timing controls. For example, although not shown in the detailed schematic, the atrial and ventricular sense amplifiers are preferably blanked for several milliseconds when pacing pulses are generated so as to avoid saturating them. (Typically, atrial blanking may be for 30 milliseconds and ventricular blanking may be for 100 milliseconds.) The system may also be programmed in a conventional manner so that the overall rate at which pacing pulses are generated decreases toward the end of the life of the pacer battery, as is known in the art. The detailed schematic is directed to what we consider to be the inventive features of our invention, and not to all possible standard pacer features which may actually be incorporated in a practical device.

Ventricular Pacing Rate Control—FIG. 2

As long as atrial beats occur in the P-wave synchrony timing window, the atria and ventricles beat in synchronism. Even if the atria do not beat spontaneously, an atrial pacing pulse is generated at the end of the P-wave synchrony timing window. Whether a spontaneous beat is detected or an atrial pacing pulse is generated, the AV delay period begins. Similarly, VA delay timing begins as soon as a ventricular beat is detected during the AV timing or a ventricular pacing pulse is generated.

If the atria would otherwise beat spontaneously at too slow a rate, an atrial pacing pulse is generated at the end of each VA delay timing interval. Assuming that ventricular pacing pulses are also generated at the end of each VA delay period, it is apparent that both types of pacing pulses occur at a rate which is the reciprocal of the sum of the six timing intervals which control the system operation; these six intervals are the AV delay interval, the atrial refractory period, the Wenckebach timing window, the P-wave synchrony timing window, and the two pulse widths. The graph of FIG. 2 depicts the ventricular pacing rate as a function of the atrial rate. The "standby" rate (e.g., 72 beats per minute) is the reciprocal of the sum of the six basic timing intervals. Atrial pacing pulses are generated (assuming that the pacer has been programmed to generate atrial pacing pulses) at a rate no lower than the standby rate, and the ventricular pacing pulses are generated at the same rate.

It will be noted that the horizontal axis of FIG. 2 is the "time" axis. A time axis is used to indicate what happens as the ventricular pacing rate is automatically lowered, as will be described below. For the moment, it is sufficient to think of the ventricular pacing rate as tracking the atrial pacing rate along the horizontal line segment labelled A.

If the atria beat spontaneously at a rate faster than the standby rate, the ventricular pacing rate follows the atrial rate since for every spontaneous atrial beat a ventricular pacing pulse is generated at the end of the AV delay interval, unless the ventricles beat spontaneously. Thus the atrial rate and ventricular pacing rate are the same along line segment B of the graph of FIG. 2.

Line segment B represents what happens when atrial beats occur within the P-wave synchrony timing window of FIG. 1. A departure in the two rates takes place when the atrial rate exceeds the Wenckebach rate shown on FIG. 2 (line segment C). This corresponds to a spontaneous atrial beat occuring prior to the start of the P-wave synchrony timing window.

It will be recalled that an atrial beat which occurs during the Wenckebach timing window does not result in the triggering of the AV delay timing interval. Instead, the system waits until the end of the Wenckebach timing window and only then does the AV delay timing begin. The effect is to lengthen the time between each spontaneous atrial beat and the next ventricular pacing pulse if a spontaneous ventricular beat is not detected; the AV delay is lengthened by the time between the sensing of the spontaneous atrial beat and the time-out of the Wenckebach window. The reason for this is that while excessively fast atrial beats do not pose a danger, excessively fast ventricular pacing can be fatal.

Obviously, since the purpose of providing the Wenckebach timing window is to prevent ventricular pacing pulses from being generated at the same rate as the atrial beats, there are fewer ventricular pacing pulses generated than there are atrial beats which are sensed. The lengthening of the effective AV delay interval results in successive atrial beats being sensed earlier and earlier during the Wenckebach timing window in successive cycles of operation. Eventually, as the atrial beats move to the left through the Wenckebach timing window of FIG. 1, an atrial beat occurs during the atrial refractory period following the last ventricular pacing pulse. This atrial beat is therefore ignored, the AV delay timing is not triggered, and a ventricular pacing pulse is skipped. Suppose, for example, that it requires nine atrial beats for the sensing of the beats to move all the way from the right end of the Wenckebach timing window past the left end of the window during successive cycles. It will be only the ninth atrial beat which does not result in the generation of a ventricular pacing pulse, and consequently there will be eight ventricular pacing pulses at the Wenckebach rate for nine atrial beats. This is known in the art as a 9:8 "block". If atrial beats are detected at a faster rate, it may require only six atrial beats for the sensing of the beats during successive cycles to move all the way through the Wenckebach timing window from the right end into the atrial refractory period. In such a case there would be a 6:5 block, with only five ventricular pacing pulses at the Wenckebach rate being generated for each six sensed atrial beats.

Referring to line segment D in FIG. 2, as the atrial rate increases above the Wenckebach rate, the ventricular pacing rate is shown as remaining constant at the Wenckebach rate. This is not an accurate representation, however, and it is for this reason that line segment D is shown by a dashed line. What actually happens is that the average ventricular pacing rate increases with the atrial rate until there is a transition, for example, from a 6:5 block to a 5:4 block. At the transition point the average ventricular pacing rate drops, but then starts to increase again as the atrial rate increases. This is a well-known phenomenon in the pacing art. The type of operation is a compromise between two conflicting requirements, those of having a ventricular contraction following each atrial contraction after the AV delay interval, but not having the ventricles beat at too fast a rate. By skipping ventricular pacing pulses at periodic intervals rather than changing the ventricular pacing rate to a lower value with no pulses being skipped, a high degree of synchronism can be maintained without the overall or average ventricular pacing rate rising to a dangerous level.

There comes a point, however, where it makes little sense to even try to maintain synchronism between atrial and ventricular beats; the atria are beating so fast that ventricular pacing at the same rate could pace the patient to death. This point is where the atrial rate rises to the "atrial upper rate" depicted in FIG. 2. Before even considering what now happens to the ventricular pacing rate, consideration must be given to how the "true" atrial rate is even determined when so many atrial beats are actually ignored since they fall in the atrial refractory period. Atrial beats should be and are ignored if they occur so soon after a ventricular beat or pacing pulse; that is the way in which the ventricular pacing rate is limited relative to the atrial rate as the latter increases. But if atrial beats which occur during the atrial refractory period are thus ignored, the "true" atrial rate cannot be determined. The problem is aggravated at high atrial rates when more and more beats occur during atrial refractory periods.

What the system does is to monitor the average atrial rate over an interval of three seconds. Operation of the atrial sense amplifier within the atrial interference reversion period is ignored because physiological atrial beats rarely occur at such a rapid rate. Similarly, operation of the atrial sense amplifier within thirty milliseconds prior to operation of the ventricular sense amplifier is discounted because it is assumed that the more sensitive atrial sense amplifier picked up a ventricular beat. (As described above, the atrial sense amplifier is also blanked for a short interval after a ventricular pacing pulse is generated; this avoids erroneous pick-up of a ventricular pacing pulse on the atrial lead.) But all other operations of the atrial sense amplifier—even those occurring during atrial refractory periods—are counted over a period of three seconds. Thereafter, the counter is reset and another count begins. It is the count at the end of each three-second interval which represents the true atrial rate. (The actual atrial rate is the final count divided by three, or the final count divided by whatever interval is used for the averaging; the interval must be long enough to permit an average value to be determined but not so long as to introduce an excessive lag in pacer response. The shorter the interval, the greater the possibility of one or two premature atrial beats resulting in an unnecessary change in the mode of operation.)

Before discussing how the ventricular pacing rate changes once the atrial rate reaches the atrial upper rate, it should be appreciated how the programmed atrial upper rate should be selected in the first place. As discussed above, as the atrial rate continuously increases above the Wenckebach rate, the ventricular pacing rate increases with it, then exhibits a sharp drop, then continues to increase with the atrial rate, etc. At the transition from a 6:5 to a 5:4 block, for example, there is not a dramatic decrease in the ventricular pacing rate. But in going from a 3:2 to a 2:1 block, there would be a dramatic decrease in ventricular pacing rate. Consider, for example, a Wenckebach rate of 130 beats per minute. With a 3:2 block, the atria beat at 130 beats per minute while the ventricles are paced at a rate of only about 87 beats per minute. But if the atria beat just slightly faster and this results in a transition to a 2:1 block, ventricular pacing pulses will be generated at a rate of only 65 pulses per minute. Such a dramatic drop in the ventricular pacing rate, especially if the patient is exercising, can give rise to considerable discomfort. Accordingly, the atrial upper rate which is selected should be such that a 2:1 block never results. While the atrial upper rate can be selected to occur between two other successive blocking conditions, it is preferred to select an atrial upper rate such that the ventricular pacing rate starts to decrease after a 3:2 block has been achieved but before a 2:1 block would otherwise result. A typical atrial upper rate is 150 beats per minute.

As soon as the atrial rate reaches the atrial upper rate, no attempt is even made to synchronize the ventricular pacing pulse to atrial beats. Instead, ventricular-ventricular timing takes place, each timing interval beginning with a spontaneous ventricular beat or the generation of a ventricular pacing pulse. If another spontaneous ventricular beat is not detected before the time-out, then a ventricular pacing pulse is generated, that is, the system operates in a conventional "demand" VVI mode. The question is what timing interval is used.

The pacer is programmed with two additional rates, the "fall-back" rate (e.g., 80 beats per minute) and the "back-up" rate (e.g., equal to the Wenckebach rate which might be 140 beats per minute). As soon as the atrial rate reaches the atrial upper rate, the back-up rate is employed. The timing interval is gradually increased until it corresponds to the lower-value fall-back rate. The decrease in ventricular pacing rate is gradual and, in the illustrative embodiment of the invention, successive ventricular pacing pulses occur after additional 20-millisecond delays. It typically requires 6–10 seconds for the ventricular pacing rate to drop from the back-up rate to the fall-back rate. The controlled decrease in ventricular pacing rate is independent of atrial beat sensing.

So that the patient does not perceive an excessive instantaneous change in pacing rate, the back-up rate should be close to the Wenckebach rate (possibly higher, as described above, so that tachycardia might be terminated), with the ventricular pacing rate then progressively declining to the fall-back rate. The fall-back rate itself is made higher than the standby rate since the pacing which now takes place is less efficient haemodynamically than that which results from dual-chamber pacing.

The reason for labelling the horizontal axis in FIG. 2 as representing "time" is that once the atrial rate exceeds the atrial upper rate, the ventricular pacing rate does not correspond to the atrial rate. Instead, the ventricular pacing rate starts decreasing along line segment E as a function of time toward the fall-back rate.

As the ventricular pacing rate decreases from the back-up rate to the fall-back rate along line segment E, the system may operate in what is known as the "tachycardia reversion mode". Whenever a ventricular pacing pulse is generated, an atrial pacing pulse is generated almost simultaneously if the pacer has been programmed to operate this way. The reason for the excessively high atrial rate in the first place is that the patient may be suffering from re-entrant tachycardia—the ventricular depolarization travels back to the atria and triggers another atrial beat. If the atria are depolarized by an atrial pacing pulse at about the same time that the ventricules beat, the re-entrant (feedback) circuit may be disrupted. Although as will be described below simultaneous pacing of this type is under program control, in the usual case it is preferred to generate atrial pacing pulses as the ventricular pacing rate drops from the back-up rate to the fall-back rate. Once the fall-back rate is reached, the atria are no longer paced and the system is operated in a standard VVI mode at the constant fall-back rate (line segment F in FIG. 2). This operation persists until the atrial rate drops below the atrial upper rate, as which time the ventricular pacing rate switches to that depicted by line segment D.

The atrial rate, as determined by the three-second counter, is also compared with a programmable minimum rate referred to as the "brady" rate. If the atrial rate drops below the brady rate, then the sensing of an atrial beat does not trigger AV delay timing; atrial-ventricular synchronism is prevented at low atrial rates because it would otherwise result in irregular ventricular pacing with negligible haemodynamic benefit.

Before proceeding to a description of FIGS. 3–5, it will be helpful to summarize the parameters which may be programmed. The six timing intervals required for the basic timing depicted in FIG. 1 are the ventricular pacing pulse width and the atrial pacing pulse width (neither of which is actually shown in FIG. 1), the AV delay, the atrial refractory period, the Wenckebach timing window and the P-wave synchrony timing window. In addition, the pacer must be programmed with values for the atrial upper rate and the atrial brady rate, and the back-up and fall-back rates.

There are also eight mode bits which are programmable and they are listed in FIG. 7 for reference purposes. Mode bit A controls whether ventricular sensing takes place while the atrial rate is below the atrial upper rate (AUR). Similarly, mode bit H determines whether ventricular sensing takes place when the atrial rate exceeds the atrial upper rate and the ventricular pacing rate is decreasing along line segment E in FIG. 2; once the rate falls to the fall-back rate, ventricular sensing cannot be disabled and the pacer operates in the VVI mode. Mode bit B determines whether atrial sensing is enabled; only one mode bit is required for this purpose because the sensing of atrial beats when the atrial rate is above the atrial upper rate has no effect on the system operation.

Mode bit C, applicable when the atrial upper rate is not exceeded, determines whether ventricular pacing is in the inhibit or synchronous mode. In the former, a ventricular pacing pulse is not generated when a ventricular beat is detected, and the VA delay timing begins without a ventricular pacing pulse being generated. When the system is operated in the synchronous mode, a ventricular pacing pulse is generated whenever a ventricular beat is detected. Mode bit G serves a similar function, but it controls whether a ventricular pacing pulse is generated together with a spontaneous ventricular beat only when the atrial rate exceeds the atrial upper rate and ventricular pacing is not occurring at the fall-back rate, i.e., along line segment E in FIG. 2.

Mode bits D and E determine whether atrial pacing takes place, each of the mode bits playing a determining role depending upon whether the atrial rate is above or below the atrial upper rate. Mode bit E is applicable only when the ventricular pacing rate is falling along line segment E of FIG. 2 (atrial pacing pulses being generated, if the pacer is so programmed, in an effort to terminate tachycardia). Once the fall-back rate has been reached, there is no atrial pacing. Mode bit F determines whether there is ventricular pacing along line segment E in FIG. 2; in some cases, atrial pacing without ventricular pacing is more effective in the treatment of tachycardia.

At the bottom of FIG. 7 three Boolean functions are shown. These functions characterize signals which control ventricular sensing, and atrial and ventricular pacing, under different conditions.

Even without referring to the detailed schematic, the three Boolean functions may be analyzed. In addition to having mode bit terms, the functions include the terms AUR, FBR and R DETECT. The AUR signal is high (AUR=1) when the atrial rate exceeds the atrial upper rate; otherwise it is low (AUR=0). The FBR signal is high (FBR=1) only when the system operation is characterized by line segment F in FIG. 2. The R DETECT signal, when high, represents the sensing of a ventricular beat.

Referring to the first equation in FIG. 7, ventricular sensing is always enabled when ventricular pacing proceeds at the fall-back rate since the system operates in the VVI mode. The function is disabling, i.e., ventricular sensing is disabled only when the function is a 1; thus, the $\overline{FBR}$ term prevents ventricular sense disablement along line segment F in FIG. 2 because FBR=1 at this time and the function is a 0. Along line segment E in FIG. 2, FBR=0 and AUR=1 so mode bit H determines whether ventricular sensing takes place; it is disabled if H=1. Similarly, along line segments A, B and D in FIG. 2, FBR=0 and $\overline{AUR}$=1 so mode bit A is the controlling factor.

The atrial pace function is enabling, that is, atrial pacing can take place only when the Boolean expression is a 1. Along line segment F in FIG. 2, when the system operates in the VVI mode, there is to be no atrial pacing. Since FBR=1, the atrial pace enable function is a 0. At all other times, $\overline{FBR}$=1. Along line segment E, AUR=1 so mode bit E is the controlling factor; along line segments A, B and D, $\overline{AUR}$=1 so mode bit D is the controlling factor.

The ventricular pace disable function comprises two terms. The first pertains to line segment E in FIG. 2, at which time $\overline{FBR}$=1 and AUR=1. If mode bit F is a 0, ventricular pacing takes place; otherwise, it is disabled. But even if ventricular pacing is enabled along line segment E, the system may still be programmed to operate in the inhibit mode in which case a sensed ventricular beat is not reinforced by ventricular pacing pulse. Similarly, while ventricular pacing cannot be totally disabled along line segments A,B, D and F, the pacer may be programmed to operate in the inhibit mode along these line segments. The second term in the ventricular pace disable function determines whether the system operates in the inhibit mode along all line segments (with the F mode bit determining whether ventricular pacing takes place at all along line segment E, as just discussed).

The first factor in the second term of the ventricular pace disable function is (R DETECT); ventricular pacing can be inhibited only if a ventricular beat is sensed. The second factor has three parts. These parts are best considered by rewriting them as $(C)(\overline{AUR})+(G)(AUR)(\overline{FBR})+(FBR)$. The C mode bit is controlling along line segments A, B and D, where $\overline{AUR}$=1. The G mode bit is controlling along line segment E, where AUR=1 and $\overline{FBR}$=1. Along line segment F the pacer is to operate in the VVI mode, and since FBR=1 ventricular pacing is disabled when a ventricular beat is sensed. The reason that the second factor in the second term of the function does not include an $\overline{(FBR)}$ component is that the expression (G)(AUR)$\overline{(FBR)}$+(FBR) reduces to (G)(AUR)+(FBR).

Illustrative Embodiment Of The Invention—FIGS. 3–5

The ventricular and atrial stimulating electrodes are shown by respective numerals 10, 20. Flip-flop 142 on FIG. 5 has its Q output connected to the input of level converter 60. While the flip-flop is in the set state with its Q output high, the level converter applies a negative pacing pulse to the atrial stimulating electrode. Similar remarks apply to flip-flop 138, level converter 62, and the ventricular stimulating electrode. Any of conventional level converters can be used in the system. It is also to be understood that conventional indifferent electrode connections are provided, although alternatively the case of the pacer may be grounded.

The ventricular stimulating electrode 10 is coupled to a conventional ventricular sense amplifier/comparator circuit 12, which circuit generates a short positive pulse whenever a ventricular beat is detected. The output of the amplifier/comparator is coupled to one input of gate 16 and to the input of ventricular interference reversion period timer 14. The latter circuit has its output connected to an inverting input of gate 16. Each detection of a ventricular beat causes the timer output to go high to disable gate 16 (after a short delay sufficient for the trigger pulse to pass through gate 16). The only pulses from amplifier/comparator 12 which pass through the gate are those which do not occur within an interference reversion period triggered by a preceding pulse.

Ventricular sense disable logic 18 is connected to another inverting input of gate 16. As long as the output of the disable logic is low, pulses representing ventricular beats appear on the R DETECT conductor connected to the output of gate 16. Whenever the sensing of ventricular beats is to be disabled, however, the output of logic circuit 18 is held high and the R DETECT conductor remains low in potential even if a ventricular beat would otherwise have been sensed. This disable logic can be completely characterized by its four inputs (including the A and H mode bits, and the AUR and FBR signals), and the applicable Boolean equation is the first of the three equations shown at the bottom of FIG. 7 and already discussed. The logic can be implemented with only a few standard gates, and many alternative designs will be apparent to those skilled in the art.

In a similar manner, atrial sense amplifier/comparator 22 and atrial interference reversion period timer 24 control the operation of gate 26, the output of the gate being pulsed whenever an atrial beat is detected, provided that the atrial beat does not occur within the 160–200 millisecond interference reversion period which follows the preceding beat. Although gate 26 is not provided with disable logic comparable to circuit 18 which is associated with gate 16, the output of gate 26 is connected to one input of gate 64. One of the other inputs to gate 64 is mode bit B. When mode bit B, the atrial sense enable signal, is low in potential, gate 64 does not pass a pulse through it to indicate the sensing of an atrial beat.

Timer 24 actually generates two pulses at two respective outputs responsive to the detection of each atrial beat. The first pulse is 160–200 milliseconds long and is the conventional interference reversion period control. The second pulse, coupled to the input of inverter 28, has a duration of only 30 milliseconds. Inverter 28, gates 30 and 36, flip-flop 38 and delay unit 40 serve to control the generation of a pulse at the output of gate 30 each time that an atrial beat is detected, provided that a ventricular beat is not detected within 30 milliseconds following the appearance of a pulse at the output of amplifier/comparator 22. It is pulses at the output of gate 30 which are counted in order to determine the atrial rate. A patient suffering from retrograde conduction will experience atrial beats following ventricular beats, the atrial beats actually being induced by the ventricular beats. These atrial beats should be counted since they are "real" atrial beats. On the other hand, it is possible for the output of amplifier/comparator 22 to be pulsed high even when atrial beats are not present. This can result from the atrial sense amplifier/comparator actually detecting a ventricular beat due to its relatively high sensitivity; the atrial sense amplifier/comparator must have a greater sensitivity than the ventricular sense amplifier/comparator because atrial signals are lower in magnitude, and the greater sensitivity can give rise to the sensing of an "atrial" beat as a result of a ventricular depolarization, even when the atria do in fact not beat. These pulses at the output of amplifier/comparator 22 should not be counted since they do not represent "real" atrial beats. The mechanism for distinguishing between the two cases depends upon the relative times at which gates 16 and 26 have their outputs pulsed high. If the output of gate 16 goes high prior to the output of gate 26 going high immediately thereafter, it is an indication of retrograde conduction and an atrial beat should be counted. On the other hand, it the output of gate 26 goes high and the output of gate 16 follows it by going high within 30 milliseconds, it is an indication that the atrial sense amplifier/comparator really detected a ventricular depolarization and an atrial beat should not be counted; it is so unlikely that there will be a ventricular beat within 30 milliseconds of a preceding atrial beat that the earlier sensing of an atrial beat is discounted.

When a ventricular beat is detected and the output of gate 16 goes high, flip-flop 38 is reset through OR gate 36. An atrial beat which then follows causes the output of inverter 28 to go low for 30 milliseconds. The pulse at the output of gate 26 sets flip-flop 38 so that its Q output goes high. At the end of the 30-millisecond pulse at the output of timer 24, the output of gate 28 goes high once again to both reset flip-flop 38 and to enable gate 30. Delay unit 40, which has a delay of about 0.5 milliseconds, has its output held high for a short interval even after flip-flop 38 resets. Consequently, gate 30 operates and its output is pulsed after the 30-millisecond timing interval. Flip-flop 38 is now reset in preparation for another cycle of operation. Should an atrial beat be sensed without the sensing of a prior ventricular beat, the operation is the same as that just described since the flip-flop is initially reset.

Now consider the case where an atrial beat is sensed within 30 milliseconds prior to the sensing of a ventricular beat. When the output of amplifier/comparator 22 goes high, the output of inverter 28 goes low to disable gate 30. Flip-flop 38 is set, but its Q output going high cannot result in a pulse at the output of gate 30 because gate 30 is now disabled; delay unit 40 prevents the application of a high input to gate 30 before the gate is actually disabled by the output of inverter 28. Should a ventricular beat not be detected within 30 milliseconds, the output of inverter 28 will go high while the output of delay unit 40 is still high and the output of gate 30 will be pulsed high. But if a ventricular beat is detected within 30 milliseconds of the atrial beat sensing, OR gate 36 will operate to reset the flip-flop before inverter 28 enables gate 30 at the end of the timing interval. Consequently, when the output of inverter 28 does finally go high, the output of delay unit 40 is low and gate 30 is not pulsed. The net effect is that an atrial "beat" which is sensed within 30-milliseconds prior to the sensing of a ventricular beat is not counted because it is not indicative of a true atrial beat. The criterion for treating the sensing of an atrial beat as a true atrial beat is that it is not followed by the sensing of a ventricular beat within 30 milliseconds.

At 3-second intervals, timer 46 resets counter 44. The counter then starts to count pulses which appear at the output of OR gate 42. The two inputs to OR gate 42 are pulses at the output of gate 30 and atrial pacing pulses at the input of level converter 60. Both types of events must be counted since they both represent atrial beats; it is assumed that each atrial pacing pulse results in an atrial beat.

The instantaneous count represented by counter 44 is applied to an input of each of comparators 48 and 50. The other input to comparator 50 is the R1 output of atrial upper rate latch 94-3, shown on FIG. 5. This latch represents the atrial upper rate discussed in connection with FIG. 2, the rate which if exceeded indicates that the ventricular pacing rate should no longer follow the atrial rate. The output of comparator 50 is high whenever the count in counter 44 exceeds the atrial upper rate.

Similarly, comparator 48 compares the count in counter 44 with the atrial brady rate (R2) which is stored in latch 94-4 on FIG. 5. Comparator 48 operates to cause its output to go high whenever the atrial brady rate exceeds the count in counter 44. If the atrial rate is so low that it does not exceed the atrial brady rate, trying to maintain atrial-ventricular synchronism is almost irrelevant because the atrial rate is too low. Were an attempt made to maintain synchronism, it would simply interfere with normal ventricular pacing. For this reason, if the atrial rate is less than the programmed atrial brady rate, atrial sensing is disabled, as will be described below.

Because the atrial beats are averaged over 3-second intervals, the two rate values represented at inputs R1 and R2 which are compared with the count in counter 44 should affect the system operation only at the end of each 3-second interval. The comparator outputs are connected to the D inputs of respective flip-flops 52 and 54. Each of the flip-flops is clocked at the end of each 3-second timing interval (the reset input of the counter should have a short input delay to allow the flip-flops to be set before the count is reset). Consequently, the Q output of each flip-flop can change at only 3-second intervals. If the AUR conductor connected to the Q output of flip-flop 54 is high, it is an indication that the atrial rate exceeds the atrial upper rate. If the BRADY conductor connected to the Q output of flip-flop 52 is high, it is an indication that the atrial rate is lower than the atrial brady rate; gate 64 is disabled from pulsing its output upon the sensing of an atrial beat.

But 152 is the main data bus in the system. The bus is used for a variety of purposes, one of which is to control the storage of programmable values in various latches. The design of programming circuits for heart pacers is well known in the art, and details of programming logic is not necessary for an understanding of the present invention. For this reason, a program decoder 80 is shown only symbolically in FIG. 4. The program decoder responds to magnetic pulses received from an external programmer and controls the storage of programmable values in the various latches. The program decoder selects a particular latch depending upon address bits transmitted from the external programmer, and enables the latch for the storage of data. The data bits themselves are applied by the program decoder to bus 152. Mode latches 92 store the eight mode bits A–H. The six latches 90-1 through 90-6 store the six main time parameters—the four depicted in FIG. 1, as well as the two pulse widths. Latches 94-1 through 94-4 store the programmable rates which have been discussed above.

Although data bus 152 allows data on the bus to be written into all of the latches during programming, only some of the latches can have their respective data applied in the reverse directions to the bus during the system cycling. Address bus 150 is the other major bus in the system, and a 3-bit address is applied to this bus by state controller 74. The three bits applied to the address bus define the system state, and they also select a particular latch which may then apply the data stored in it to data bus 152. Address decoder 88 decodes six respective addresses to select one of latches 90-1 through 90-6 for application of the respective latched time value of the data bus, the selected value then remaining on the data bus. (In actual practice, the output of decoder 80 would enable respective tri-state buffers connected between the latches and bus 152, although for the sake of simplicity the latches are simply shown as being "selected".) Address decoder 88 also decodes a respective 3-bit address on address bus 150 to energize the enabling lead for the set of tri-state buffers 98 connected to the outputs of counter 96, so that the count in the counter appears on the data bus.

It is the state controller 74 which controls the overall system operation, as depicted by the state diagrams of FIGS. 8 and 9. The state controller defines a plurality of states, each of which is represented by a 3-bit value. The same bits which represent the state of the system are applied to several address decoders over bus 150 so that each address decoder can control the operation of respective parts of the system when the system is in a particular state. The state controller cycling will be described below in connection with FIGS. 8 and 9 but, before proceeding to a description of the state cycling, it will be helpful to understand the operation of the individual circuits and blocks in the system.

As described above, FIG. 1 depicts the basic system timing. The main system timer is presettable counter 116. Each time that the system changes state and a new address is applied to the input of address decoder 88 by state controller 74, the address decoder pulses conductor 154. This conductor is connected to the preset input of counter 116. At that time, any data which appears on data bus 152 is preset in counter 116. The data is derived from one of latches 90-1 through 90-6 or from counter 96 (when buffers 98 are enabled). Clock 114 continuously decrements the count in counter 116 after it is initially preset. When the count is decremented down to zero, the output of the counter is pulsed to energize the "end of delay" input of the state controller. For example, at the start of the atrial refractory period, the state controller applies address bits 001 to address bus 150, and address decoder 88 enables latch 90-4 to apply the data bits stored in it to data bus 152, these data bits representing the atrial refractory period. At the same time, the present input of counter 116 is pulsed so that the atrial refractory period value is stored in counter 116. The end-of-delay input of the state controller is thereafter pulsed at a time dependent upon the value of the atrial refractory period. In this way, the same presettable counter can be used to time all intervals, depending upon the value which is initially preset in it.

The only exceptions concern the atrial and ventricular pulse widths. When the system is in state 000 a ventricular pacing pulse is generated, and when it is in state 100 an atrial pacing pulse is generated. Address decoder 118 decodes these two addresses and energizes a respective one of the V PACE and A PACE outputs. Both outputs are connected to inputs of OR gate 120, whose output is connected to the disable input of counter 116. Thus in these two states counter 116 does not have its count decremented under control of clock 114. Another mechanism is provided to indicate that a pacing pulse has been generated and that the system can advance to the next state, as will be described below.

When the AUR conductor is high to indicate that the atrial rate exceeds the Wenckebach rate, the AUR input of state controller 74 is high to indicate that the ventricular pacing rate should no longer follow the atrial rate. This condition is represented in the drawing as AUR=1 and FIG. 9 characterizes the system cycling in such a case. When AUR=0, the atrial rate does not exceed the Wenckebach rate and the ventricular pacing rate should be synchronized to the atrial rate. FIG. 8 is the state diagram for this case. It is only when AUR=0 that counter 116 is used to time the four intervals represented in FIG. 1 (AV delay, atrial refractory period, Wenckebach timing window and P-wave synchrony timing window) and that the data contained in one of latches 90-3 through 90-6 is counted down in counter 116. Referring to FIG. 8, the four states during which the respective count-downs occur are states 101, 001, 010 and 011.

When the AUR conductor goes high, on the other hand, the previously enabled (via inverter 110) preset input of counter 96 is disabled and the value stored in back-up rate latch 94-1 which is present in the counter can now be decremented. It wil be recalled that the back-up rate is the rate at which ventricular pacing begins when the atrial rate rises to the atrial upper rate. As shown in FIG. 2, the back-up rate is usually made euqal to the Wenckebach rate (although it can be different). Whenever address decoder 118 energizes its V PACE output, counter 96 is clocked and the count stored in the counter is incremented. All that occurs when AUR=1 is that ventricular pacing pulses are generated on a demand basis. The ventricular-ventricular timing interval is represented by the count in counter 96, the count being applied to data bus 152 through buffers 98 for storage in counter 116 which then controls the timing in the usual way. It is by way of incrementing the count in counter 96 each time that address decoder 118 determines that a ventricular pacing pulse is to be generated that the V—V period is lengthed from cycle to cycle.

The count in counter 96 is applied to one set of inputs of comparator 112, the other set of inputs being derived from fall-back rate latch 94-2. When the count in counter 96 has been incremented up to represent the fall-back rate, the output of comparator 112 goes high. This FBR (fall-back rate) output is applied to the inhibit input of counter 96. Thus after the ventricular pacing rate has dropped down to the fall-back rate indicated in FIG. 2, counter 96 is no longer incremented each time that the V PACE output of address decoder 118 goes high, and a constant value is maintained in counter 96. Since this value represents the fall-back rate and it is continuously loaded into counter 116 whenever address decoder 88 determines that a new V—V timing interval must begin, ventricular pulses are generated at the constant fall-back rate.

It is to be appreciated that while the rate latches represent rates, they actually store the reciprocal values, time intervals. That is why an increasing count in counter 96, which requires a longer count-down in counter 116, represents a decreasing rate. For the same reason, while the fall-back rate is lower than the back-up rate, the time interval value stored in latch 94-2 is greater than that stored in latch 94-1. It is thus an increasing count in counter 96 that eventually equals the value stored in latch 94-2.

Whenever the system enters state 000 (FIG. 8) and a ventricular pulse is to be generated, the V PACE output of address decoder 118 goes high and flip-flop 86 is reset. At the end of the generation of the ventricular pacing pulse, the reset input to flip-flop 86 goes low. The flip-flop serves to detect the occurrence of an atrial beat so that the AV delay timing can begin. It will be recalled from FIG. 1, however, that the AV delay timing should begin immediately if an atrial beat is detected during the P-wave synchrony timing window, but it should begin only at the end of the Wenckebach timing window if the beat is detected during this window. During the P-wave synchrony timing window, address bits 011 on address but 150 cause the output of address decoder 72 to be high. Not only is gate 76 enabled, but gate 64 is enabled as well through OR gate 68. Provided that the BRADY output of flip-flop 52 is low (indicating that the atrial rate is not so low that atrial beats should be ignored insofar as ventricular pulse timing is concerned), and provided that the B mode latch is high (indicating that atrial sensing has been enabled—see FIG. 7), three inputs to gate 64 are enabled. Each pulsing of gate 26 indicative of an atrial beat thus results in a pulse appearing at the output of gate 64 and the setting of flip-flop 86.

When the system is in state 010 (FIG. 8) and Wenckebach timing is in progress, the output of address decoder 70 is high. This output is connected to a second input of OR gate 68, so that gate 64 is enabled just as it is during P-wave synchrony timing. Once again, flip-flop 86 is set as soon as an atrial beat is detected. But gate 76 does not operate, even though the Q output of the flip-flop is high, until the system cycles to state 011 and address decoder 72 enables its output. Thus it is apparent that gate 76 operates simultaneously with the detection of an atrial beat if it occurs during the P-wave synchrony timing window, but the gate operates only at the end of the Wenckebach timing window if the atrial beat is detected during this window. Delay 78 is provided only so that pulsing of the AV delay trigger input of the state controller is delayed slightly when the system enters state 011 with the operation of address decoder 72, in order that the system settle down at the start of the P-wave synchrony timing before an AV delay trigger is generated. If an atrial beat is detected during the Wenckebach timing window, the system enters the P-wave synchrony timing state 011, but cycles out of this state about one millisecond later after delay unit 78 energizes the AV delay trigger input of the state controller.

During ventricular pacing pulse and atrial pacing pulse timing, one of the V PACE or A PACE outputs of address decoder 118 is high; since both outputs are connected to inputs of OR gate 120, the output of the OR gate is high. Inverter 122 normally energizes the reset input of 2-millisecond counter 124, but whenever a pacing pulse is required the output of inverter 122 goes low and the counter commences a 2-millisecond timing cycle. At the end of the 2-millisecond interval, the counter pulses its output and thus energizes the "end of pace" input of the state controller. This causes the state controller to cycle to the next state, the required atrial or ventricular pacing pulse having been generated.

However, the width of the pulse which is generated is not controlled by counter 124. All pulses are less than 2 milliseconds in width. The system remains in a state in which a pacing pulse is generated for two milliseconds, but the width of the pulse is actually controlled by comparator 130. As counter 124 times its 2-millisecond interval, its count is continuously incremented and the count is applied to one input of comparator 130. The other input of the comparator is connected to data bus 152, on which there appears a value representative of the ventricular pacing pulse width or the atrial pacing pulse width. Address decoder 88 enables one of latches 90-1 or 90-2 so that the respective pulse width value appears on the data bus. As soon as comparator 130 determines that the count in counter 124 has advanced to the value represented on the data bus, the comparator output goes high to signal that the pulse in progress should be terminated.

When a ventricular pacing pulse is to be generated and the V PACE output of address decoder 118 first goes high, flip-flop 138 is clocked. At this time, because its D input is connected to a positive potential, the Q output goes high. As described above, when the Q output of flip-flop 138 is high, a ventricular pacing pulse is generated. When the output of comparator 130 goes high, a pulse is transmitted through OR gate 136 to the reset input of the flip-flop so that the Q output goes low, thus terminating the pulse. Even though the ventricular pacing pulse terminates before the end of the 2-millisecond timing interval of counter 124, the system remains in the same state until the end of the timing interval (which is so short that it is of no moment). Ventricular pace disable logic 134 has its output connected to the other input of OR gate 136; as long as the output of logic circuit 134 is high, ventricular pacing pulses cannot be generated because the reset inut of flip-flop 138 causes the Q output to remain low. The Boolean equation which defines the operation of ventricular pace disable logic 134 is shown at the bottom of FIG. 7, and has been discussed above.

In a similar manner, whenever an atrial pacing pulse is required, address decoder 118 causes its A PACE output to be high. When this output of the address decoder first goes high, flip-flop 142 is clocked and its Q output goes high to control the generation of an atrial pacing pulse. The pulse is terminated in a comparable manner when the output of comparator 130 goes high and gate 140 resets the flip-flop, after counter 124 has counted to a count equal to the atrial pacing pulse width which appears on data bus 152. Atrial pace enable logic 132 has its output connected to the inverting input of gate 140. If the output of logic circuit 132 is low, the reset input of flip-flop 142 is held high and the Q output of the flip-flop is held low, thus preventing the generation of an atrial pacing pulse. The Boolean equation which defines the atrial pace enable logic is also depicted in FIG. 7, and has been discussed above.

State Diagrams—FIGS. 8 and 9

The state diagram of FIG. 8 depicts the system cycling when AUR=0. Referring to FIG. 2, this corresponds to any atrial rate which is below the atrial upper rate. The timing described above with respect to FIG. 1 characterizes the system operation at this time. It should be appreciated that once the atrial rate exceeds the Wenckebach rate, ventricular pacing is controlled not only by the state controller, but also by the circuitry which includes gate 76 and flip-flop 86 which delay the generation of an AV delay trigger input to the state controller until after the Wenckebach timing is over, that is, until address decoder 72 signals the start of the P-wave synchrony tiing window. Thus the state diagram of FIG. 8 need not account for when an atrial beat is detected; it is the generation of an AV delay trigger which affects the state controller, and it is gate 76, flip-flop 86 and the related circuits which control when the AV delay trigger is actually generated.

Referring to FIG. 8, assume that the system is in state 000, during which time a ventricular pacing pulse is generated. The width of the pulse is controlled by comparator 130 and the ventricular pacing pulse width value which is applied to data bus 152 by latch 90-1. The pulse actually terminates before the end of the 2-millisecond time-out of counter 124. But it is only at the end of the time-out that the "end of pace" input to the state controller goes high and the system cycles from state 000 to state 001. As soon as the system enters state 001, the atrial refractory period begins, as shown in FIG. 1. The value stored in latch 90-4 is loaded into counter 116, and during the atrial refractory period timing the system does not change state as a result of any external atrial signal which is detected. At the end of the atrial refractory period timing, when counter 116 pulses its output, that is, the "end of delay" input of the state controller, the system cycles from state 001 to state 010.

As soon as the system enters state 010, the timing value stored in latch 90-6 is loaded into counter 116 and the Wenckebach timing interval commences. Once again, the system state does not change as a result of any external signals; it is only when the end-of-delay signal is generated after the count in counter 116 is decremented down to zero that the system switches to state 011. Of course, if an atrial beat is detected during the Wenckebach timing window, flip-flop 86 is set as described above. However, gate 76 is not enabled until the system enters state 011, at which time address decoder 72 operates.

Once the system is in state 011, as indicated in FIG. 8 it can switch out of this state in three ways. Although the pacer is designed for dual chamber operation, the physician may decide that atrial pacing is not called for. It is mode bit D which determines whether atrial pacing takes place when AUR=0, as shown in FIG. 7. At the start of the P-wave synchrony timing, the value stored in latch 90-5 is applied to data bus 152, and at the end of the P-wave synchrony timing window the end-of-delay input to the state controller is energized. As shown in FIG. 8, and assuming that the D mode bit is 0, the system switches to state 000, at which time a ventricular pacing pulse is generated.

On the other hand, if the D mode bit is 1, indicating that the atrial pacing is required, then when counter 116 counts down to zero and the end-of-delay signal is generated, the system switches from state 011 to state 100, as shown in FIG. 8. It is during this state that an atrial pacing pulse is generated, under control of comparator 130. Of course, during state 100 it is latch 90-2 which is coupled to data bus 152 instead of latch 90-1. Counter 124 pulses the end-of-pace input to the state controller in the usual way to control a transition from state 100 to state 101.

As shown in FIG. 8, it is in state 101 that the AV delay timing beings. But the system need not enter state 100 in going from state 011 to state 101. An atrial pacing pulse is required only if an atrial beat is not detected within the P-wave synchrony timing window. If such a beat is detected, represented by an AV delay trigger pulse at the output of delay unit 78, the system cycles directly to state 101 from state 011 and an atrial pacing pulse is not generated. Instead, AV delay timing begins.

Even if the D mode bit is 0, an AV delay trigger input causes a transition from state 011 to state 101. This assumes, of course, that the B mode bit is 1 so that atrial sensing is enabled in the first place (see gate 64 on FIG. 3). If atrial sensing is not enabled (B=0) and atrial pacing is disabled (D=0), the system cannot enter state 101 and there is no AV delay timing. In such a case, the VA delay (states 001, 010 and 011) should be relatively long.

At the end of the AV delay timing interval, if AV delay timing takes place, the end-of-delay input to the state controller is energized by counter 116 and the system enters state 000, at which time a ventricular pacing pulse is generated.

Two other inputs in FIG. 8 should be considered. The first is the R DETECT signal from gate 16 in FIG. 3. Whenever a ventricular beat is detected, no matter what the present state of the system, it enters state 000—provided mode bit A is a 0 so that ventricular sensing is not disabled; this is the starting point for all system timing. The system enters state 000 not only from state 101 or state 011 when a ventricular pacing pulse is required, but also whenever a ventricular beat is detected. In the latter case, a reinforcing pacing pulse may or may not be generated, depending on the value of the C mode bit as described above.

Also shown in FIG. 8 is state 110; this is a state in which the system finds itself when AUR=1 and it is the state which controls the basic ventricular-ventricular pacing pulse timing when the atrial rate is too high and the system does not even attempt to maintain synchronism between atrial beats and ventricular pacing. The dashed transition line in FIG. 8 from state 110 to state 000 represents the only possible transition from the state diagram of FIG. 9 to the state diagram of FIG. 8. If AUR=1 and the state diagram of FIG. 9 controls the system operation, the system does not switch to the cycling depicted in FIG. 8—even if the AUR conductor goes low—until the system exits state 110. With the generation of the end-of-delay input to the state controller, the system switches from state 110 in FIG. 9 to state 000 in FIG. 8 provided that the AUR conductor has gone low. Referring to FIG. 2, it is apparent that the transition from the state diagram of FIG. 9 to that of FIG. 8 will usually occur while the atrial rate is still above the Wenckebach rate, the atrial rate now having fallen below the atrial upper rate with the AUR conductor having gone low. After a ventricular pacing pulse is generated, the state cycling begins with the atrial refractory period timing (state 001) when the end-of-pace signal is generated by counter 124.

The state diagram of FIG. 9 depicts the system cycling when AUR=1, that is, the atrial rate is greater than the atrial upper rate as shown in FIG. 2. The state diagram of FIG. 9 depicts four states 001, 010, 011 and 101 which are not directly involved in the normal system cycling when AUR=1. These states are shown with dashed lines representing state transitions, only to indicate how the system switches from being controlled in accordance with the state diagram of FIG. 8 to being controlled in accordance with the state diagram of FIG. 9. When the system is in any one of the four states just mentioned, the state diagram of FIG. 8 controls even though AUR=1. It is only after the system enters either state 000 or state 100 in accordance with the state diagram of FIG. 8 that the system cycling proceeds in accordance with the solid-line transitions shown in the state diagram of FIG. 9. At this time, the only states whch control the system are states 000, 110 and 100.

The system spends most of its time in state 110, the state in which V-V timing takes place. It is the V-V period which, of course, determines the ventricular pacing rate. At the end of the V-V timing when the output of counter 116 is pulsed to energize the end-of-delay input of the state controller, the system enters state 100. During this state, whose duration is 2 milliseconds under control of counter 124, an atrial pacing pulse is generated if the E mode bit is 1 and FBR=0 (see the atrial pace enable function of FIG. 7). The duration of the pacing pulse is a function of the value stored in latch 90-2. At the end of the 2-millisecond interval, with the energization of the end-of-pace input of the state controller, the system switches to state 000. At this time a ventricular pacing pulse is generated depending upon the states of the FBR and R DETECT signals, and the F and G mode bits (see the ventricular pace disable function of FIG. 7). The duration of the pulse is controlled by the value stored in latch 90-1, although the state actually persists for 2 milliseconds under control of counter 124. With the energization of the end-of-pace input of the state controller by counter 124, the system switches back to state 110, at which time another V-V timing interval begins. No matter what the state of the system, it switches to state 100 upon the detection of a ventricular beat—if the FBR signal is high (line segment F in FIG. 2), or if the FBR signal is low (line segment E) and the H mode bit is a 0—as is evident from the ventricular sense disable function of FIG. 7.

It should be noted that whenever the system is in state 110 and address bits 110 appear on bus 150, address decoder 88 enables buffers 98 so that the count in counter 96 appears on data bus 152. It is the value in this counter which is preset into counter 116 and controls the V-V timing period. Counter 96 is initially set with the value of the back-up rate when the AUR conductor first goes high and the preset input is de-energized. Thereafter, address decoder 118, which energizes its V PACE output whenever a ventricular pacing pulse is to be generated, increments the count in counter 96 so that successive V-V timing intervals get longer and longer. It is only when the FBR conductor goes high, that is, when the value in counter 96 represents the fall-back rate, that counter 96 is no longer incremented. It is in this way that the ventricular pacing rate is slowly decreased and then caused to stay equal to the fall-back rate without any need for the state controller to "know" exactly what is going on. The state controller simply causes buffers 98 to be enabled whenever the system is in state 110, and it is the external circuitry which actually determines the ventricular pacing rate.

The E mode bit determines whether atrial pacing takes place as the ventricular pacing rate is falling along line segment E in FIG. 2. It is only in this region of ventricular pacing that the FBR signal is low and the AUR signal is high, so that the atrial pace enable function of FIG. 7 is determined by the E mode bit. According to the state diagram of FIG. 9, the system is placed in state 100 both at the end of a V-V timing interval and whenever a ventricular beat is detected (assuming that the ventricular sense disable function is low). During normal VVI operation at the fall-back rate (line segment F of FIG. 2), atrial pacing is not enabled because the FBR signal is high. But as the ventricular pacing rate is being reduced before the fall-back rate is reached, each time that the system enters state 100 an atrial pacing pulse can be generated—following the generation of a ventricular pacing pulse (as the system exits state 110) or responsive to the detection of a spontaneous ventricular beat (if the ventricular sense disable signal is low). The ventricular pacing rate is decreasing in the first place because the atrial rate has risen above the atrial upper rate. This may be an indication of tachycardia, and it may be possible to terminate the condition by pacing the atria almost simultaneously with the occurrence of a ventricular beat or the pacing of the ventricles, the pacing of the atria disrupting the feedback path within the patient's heart which may be giving rise to tachycardia in the first place. It is for this reason that it is highly preferred that the E mode bit be a 1; as the ventricular pacing rate is decreasing from the nominal Wenckebach rate to the fall-back rate, atrial pacing pulses occur more or less simultaneously with ventricular beats, either spontaneous beats or those stimulated by ventricular pacing pulses.

Along line segment E of FIG. 2, ventricular pacing can be disabled under control of the F mode bit. It it is, there will be no ventricular pacing for several seconds until counter 96 is incremented up to represent the fall-back rate. In some cases, it may be more effective in the treatment of tachycardia to allow only atrial pacing along line segment E.

As described above, once pacing pulses are being generated at the constant fall-back rate, they continue to be so generated until the atrial rate drops below the atrial upper rate. It is possible to delay this switchover to normal operation until the atrial rate actually falls below the atrial upper rate by about 20 beats per minute. Such a hysteresis effect would prevent spurious changes between the two modes of operation if the atrial rate is hovering around the atrial upper rate. To provide this modification some additional logic would be required, for example, useof a comparator for comparing the atrial rate with another threshold value. another threshold value.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A heart pacer comprising means for sensing atrial beats; means for generating ventricular pacing pulses; means responsive to said atrial beat sensing means for determining the atrial rate as a function of the number of atrial beats which occur during a mesurement interval which is sufficiently long to allow an average value to be determined; and means for controlling said ventricular pulse generating means to operate in synchronism with said atrial beat sensing means when said atrial rate is below a predetermined atrial upper rate, for controlling said ventricular pulse generating means to operate at a constant rate independent of said atrial beat sensing means when said atrial rate is above said predetermined atrial upper rate, and for controlling the operating rate of said ventricular pulse generating means to decrease gradually toward said constant rate following said atrial rate first rising above said predetermined atrial upper rate.

2. A heart pacer in accordance with claim 1 wherein said controlling means causes the ratio of the number of sensed atrial beats to the number of generated ventricular pacing pulses to equal N:(N−1), with N decreasing as the rate at which atrial beats are sensed increases, while said atrial rate is still below but is in the vicinity of said predetermined atrial upper rate; and said controlling means causes the operating rate of said ventricular pulse generating means to start reducing gradually before said ratio has reached 2:1.

3. A heart pacer in accordance with claim 2 wherein said controlling means causes the operating rate of said ventricular pulse generating means to start reducing gradually after said ratio has reached 3:2.

4. A heart pacer in accordance with claim 2 wherein said controlling means limits the minimum operating rate of said ventricular pulse generating means to a standby value, and said constant rate is higher than said standby value.

5. A heart pacer in accordance with claim 4 further including means under external control for setting the initial rate at which said ventricular pulse generating means first operates when said atrial rate first rises above said predetermined atrial upper rate, the operating rate of said ventricular pulse generating means then decreasing gradually from said initial rate to said constant rate.

6. A heart pacer in accordance with claim 5 further including means under external control for setting said predetermined atrial upper rate.

7. A heart pacer in accordance with claim 2 wherein said controlling means causes the time intervals between successive pacing pulses generated by said ventricular pulse generating means to increase in equal increments as its rate of operation decreases gradually.

8. A heart pacer in accordance with claim 7 further including means for generating atrial pacing pulses, and means for controlling an atrial pacing pulse to be generated approximately simultaneously with each generated ventricular pacing pulse during the time that the operating rate of said ventricular pulse generating means decreases gradually.

9. A heart pacer in accordance with claim 8 further including means for inhibiting operation of said atrial pulse generating means while said ventricular pulse generating means operates at said constant rate.

10. A heart pacer in accordance with claim 2 further inluding means for preventing the operation of said ventricular pulse generating means to be synchronized to the sensing of atrial beats when said atrial rate falls below a value indicative of bradycardia.

11. A heart pacer in accordance with claim 10 further including means for sensing ventricular beats, means for generating atrial pacing pulses, means for synchronizing the operation of said atrial pulse generating means to the operation of said ventricular beat sensing means, and means for inhibiting operation of said atrial pulse generating means when said ventricular pulse generating means operates at said constant rate.

12. A heart pacer in accordance with claim 11 wherein said atrial pulse generating means operates approximately simultaneously with said ventricular pulse generating means during the time that the operating rate of the latter is caused to decrease gradually.

13. A heart pacer in accordance with claim 2 wherein, following operation of said ventricular pulse generating means at said constant rate, said controlling means causes operation at said constant rate to persist until said atrial rate falls below said predetermined atrial upper rate at which time said ventricular pulse generating means once again operates in synchronism with said atrial beat sensing means.

14. A heart pacer in accordance with claim 2 wherein said controlling means, in controlling said ventricular pulse generating means to operate in synchronism with said atrial beat sensing means, ignores the sensing of any atrial beat which occurs during a refractory period which follows an operation of said ventricular pulse generating means.

15. A heart pacer in accordance with claim 14 wherein said atrial rate determining means includes in its determination of atrial rate an atrial beat which is sensed during said refractory period.

16. A heart pacer in accordance with claim 15 further including means for sensing ventricular beats, and means for preventing said atrial rate determining means from including in its determination of atrial rate any sensed atrial beat which precedes a sensed ventricular beat by less than a predetermined interval.

17. A heart pacer in accordance with claim 1 wherein said controlling means limits the minimum operating rate of said ventricular pulse generating means to a standby value, and said constant rate is higher than said standby value.

18. A heart pacer in accordance with claim 1 further including means under external control for setting the initial rate at which said ventricular pulse generating means first operates when said atrial rate first rises above said predetermined atrial upper rate, the operating rate of said ventricular pulse generating means then decreasing gradually from said initial rate to said constant rate, said initial rate being settable to a value higher than that at which said vantricular pulse generating means operates when said atrial rate first rises above said predetermined atrial upper rate.

19. A heart pacer in accordance with claim 1 further including means under external control for setting said predetermined atrial upper rate.

20. A heart pacer in accordance with claim 1 wherein said controlling means causes the time intervals between successive pacing pulses generated by said ventricular pulse generating means to increase in equal increments as its rate of operation decreases gradually.

21. A heart pacer in accordance with claim 1 further including means for generating atrial pacing pulses, and means for controlling an atrial pacing pulse to be generated approximately simultaneously with each generated ventricular pacing pulse during the time that the operating rate of said ventricular pulse generating means decreases gradually.

22. A heart pacer in accordance with claim 21 further including means for inhibiting operation of said atrial pulse generating means while said ventricular pulse generating means operates at said constant rate.

23. A heart pacer in accordance with claim 1 further including means for preventing the operation of said ventricular pulse generating means to be synchronized to the sensing of atrial beats when said atrial rate falls below a predetermined minimum value.

24. A heart pacer in accordance with claim 1 further including means for sensing ventricular beats, means for generating atrial pacing pulses, means for synchronizing the operation of said atrial pulse generating means to the operation of said ventricular beat sensing means, and means for inhibiting operation of said atrial pulse generating means when said ventricular pulse generating means operates at said constant rate.

25. A heart pacer in accordance with claim 24 wherein said atrial pulse generating means operates approximately simultaneously with said ventricular pulse generating means during the time that the operating rate of the latter is caused to decrease gradually.

26. A heart pacer in accordance with claim 1 wherein, following operation of said ventricular pulse generating means at said constant rate, said controlling means causes operation at said constant rate to persist until said atrial rate falls below said predetermined atrial upper rate at which time said ventricular pulse generating means once again operates in synchronism with said atrial beat sensing means.

27. A heart pacer in accordance with claim 1 wherein said controlling means, in controlling said ventricular pulse generating means to operate in synchronism with said atrial beat sensing means, ignores the sensing of any atrial beat which occurs during a refractory period which follows an operation of said ventricular pulse generating means.

28. A heart pacer in accordance with claim 27 wherein said atrial rate determining means includes in its determination of atrial rate an atrial beat which is sensed during said refractory period.

29. A heart pacer in accordance with claim 28 further including means for sensing ventricular beats, and means for preventing said atrial rate determining means from including in its determination of atrial rate any sensed atrial beat which precedes a sensed ventricular beat by less than a predetermined interval.

30. A heart pacer comprising means for sensing atrial beats; means for generating ventricular pacing pulses; means responsive to said atrial beat sensing means for determining the atrial rate as a function of the number of atrial beats which occur during a measurement interval which is sufficiently long to allow an average value to be determined; and means for controlling said ventricular pulse generating means to operate in synchronism with said atrial beat sensing means when said atrial rate is below a predetermined atrial upper rate, for controlling said ventricular pulse generating means to operate at a constant rate independent of said atrial beat sensing means when said atrial rate is above said predetermined atrial upper rate, and for limiting the minimum operating rate of said ventricular pulse generating means to a standby value, said constant rate being higher than said standby value.

31. A heart pacer comprising means for sensing atrial beats; means for generating ventricular pacing pulses; means responsive to said atrial beat sensing means for determining the atrial rate as a function of the number of atrial beats which occur during a measurement interval which is sufficiently long to allow an average value to be determined; means for controlling said ventricular pulse generating means to operate in synchronism with said atrial beat sensing means when said atrial rate is below a predetermined atrial upper rate, and for controlling said ventricular pulse generating means to operate at a constant rate independent of said atrial beat sensing means when said atrial rate is above said predetermined atrial upper rate; and means under external control for setting said predetermined atrial upper rate.

32. A heart pacer comrising means for sensing atrial beats; means for generating ventricular pacing pulses; means responsive to said atrial beat sensing means for determining the atrial rate as a function of the number of atrial beats which occur during a measurement interval which is sufficiently long to allow an average value to be determined; means for controlling said ventricular pulse generating means to operate in synchronism with said atrial beat sensing means when said atrial rate is below a predetermined atrial upper rate, and for controlling said ventricular pulse generating means to operate at a constant rate independent of said atrial beat sensing means when said atrial rate is above said predetermined atrial upper rate; means for sensing ventricular beats; means for generating atrial pacing pulses; means for syncrhonizing the operation of said atrial pulse generating means to the operation of said ventricular beat sensing means; and means for inhibiting operation of said atrial pulse generating means when said ventricular pulse generating means operates at said constant rate.

33. A heart pacer comprising means for sensing atrial beats; means for generating ventricular pacing pulses; means responsive to said atrial beat sensing means for determining the atrial rate as a function of the number of atrial beats which occur during a measurement interval which is sufficiently long to allow an average value to be determined; and means for controlling said ventricular pulse generating means to operate in synchronism with said atrial beat sensing means when said atrial rate is below a predetermined atrial upper rate, and for controlling said ventricular pulse generating means to operate at a constant rate independent of said atrial beat sensing means when said atrial rate is above said predetermined atrial upper rate; wherein said controlling means, in controlling said ventricular pulse generating means to operate in synchronism with said atrial beat sensing means, ignores the sensing of any atrial beat which occurs during a refractory period which follows an operation of said ventricular pulse generating means.

34. A heart pacer comprising means for sensing atrial beats; means for generating ventricular pacing pulses; means responsive to said atrial beat sensing means for determining the atrial rate as a function of the number of atrial beats which occur during a measurement interval which is sufficiently long to allow an average value to be determined; and means for controlling said ventricular pulse generating means to operate in synchronism with said atrial beat sensing means when said atrial rate is below a predetermined atrial upper rate, and for controlling said ventricular pulse generating means to operate at a constant rate independent of said atrial beat sensing means when said atrial rate is above said predetermined atrial upper rate; wherein said atrial rate determining means includes in its determination of atrial rate an atrial beat which is sensed during said refractory period.

35. A heart pacer in accordance with claim 34 further including means for sensing ventricular beats, and means for preventing said atrial rate determining means from including in its determination of atrial rate any sensed atrial beat which precedes a sensed ventricular beat by less than a predetermined interval.

36. A heart pacer comprising means for sensing atrial beats; means for generating ventricular pacing pulses; means responsive to said atrial beat sensing means for determining the atrial rate; and means for controlling said ventricular pulse generating means to operate in synchronism with said atrial beat sensing means when said atrial rate is below a predetermined atrial upper rate, and for controlling the operating rate of said ventricular pulse generating means to decrease over at least several seconds to a constant rate independent of said atrial beat sensing means when said atrial rate rises above said predetermined atrial upper rate.

37. A heart pacer in accordance with claim 36 wherein said controlling means causes the ratio of the number of sensed atrial beats to the number of generated ventricular pacing pulses to equal $N:(N-1)$, with N decreasing as the rate at which atrial beats are sensed increases, while said atrial rate is still below but is in the vicinity of said predetermined atrial upper rate; and said controlling means causes the operating rate of said ventricular pulse generating means to start decreasing before said ratio has reached 2:1.

38. A heart pacer in accordance with claim 37 wherein said controlling means causes the operating rate of said ventricular pulse generating means to start decreasing after said ratio has reach 3:2.

39. A heart pacer in accordance with claim 37 wherein said controlling means limits the minimum operating rate of said ventricular pulse generating means to a standby value, and said constant rate is higher than said standby value.

40. A heart pacer in accordance with claim 37 further including means under external control for setting the initial rate at which said ventricular pulse generating means first operates when said atrial rate first rises above said predetermined atrial upper rate, the operating rate of said ventricular pulse generating means then decreasing from said initial rate to said constant rate.

41. A heart pacer in accordance with claim 37 further including means under external control for setting said predetermined atrial upper rate.

42. A heart pacer in accordance with claim 37 wherein said controlling means causes the time intervals between successive pacing pulses generated by said ventricular pulse generating means to increase in equal increments as its rate of operation decreases.

43. A heart pacer in accordance with claim 42 further including means for generating atrial pacing pulses, and means for controlling an atrial pacing pulse to be generated approximately simultaneously with each generated ventricular pacing pulse during the time that the operating rate of said ventricular pulse generating means decreases.

44. A heart pacer in accordance with claim 43 further including means for inhibiting operation of said atrial pulse generating means while said ventricular pulse generating means operates at said constant rate.

45. A heart pacer in accordance with claim 37 further including means for preventing the operation of said ventricular pulse generating means to be synchronized to the sensing of atrial beats when said atrial rate falls below a value indicative of bradycardia.

46. A heart pacer in accordance with claim 37 further including means for sensing ventricular beats, means for generating atrial pacing pulses, means for synchronizing the operation of said atrial pulse generating means to the operation of said ventricular beat sensing means, and means for inhibiting operation of said atrial pulse generating means when said ventricular pulse generating means operates at said constant rate.

47. A heart pacer in accordance with claim 46 wherein said atrial pulse generating means operates approximately simultaneously with said ventricular beat sensing means during the time that the operating rate of said ventricular pulse generating means is caused to decrease.

48. A heart pacer in accordance with claim 37 wherein, following operation of said ventricular pulse generating means at said constant rate, said controlling means causes operation at said constant rate to persist until said atrial rate falls below said predetermined atrial upper rate at which time said ventricular pulse generating means once again operates in synchronism with said atrial beat sensing means.

49. A heart pacer in accordance with claim 37 wherein said controlling means, in controlling said ventricular pulse generating means to operate in synchronism with said atrial beat sensing means, ignores the sensing of any atrial beat which occurs during a refractory period which follows an operation of said ventricular pulse generating means.

50. A heart pacer in accordance with claim 49 wherein said atrial rate determining means includes in its determination of atrial rate an atrial beat which is sensed during said refractory period.

51. A heart pacer in accordance with claim 50 further including means for sensing ventricular beats, and means for preventing said atrial rate determining means from including in its determination of atrial rate any sensed atrial beat which precedes a sensed ventricular beat by less than a predetermined interval.

52. A heart pacer in accordance with claim 36 wherein said controlling means limits the minimum operating rate of said ventricular pulse generating means to a standby value, and said constant rate is higher than said standby value.

53. A heart pacer in accordance with claim 36 further including means under external control for setting the initial rate at which said ventricular pulse generating means first operates when said atrial rate first rises above said predetermined atrial upper rate, the operating rate of said ventricular pulse generating means then decreasing from said initial rate to said constant rate, said initial rate being settable to a value higher than that at which said ventricular pulse generating means operates when said atrial rate first rises above said predetermined atrial upper rate.

54. A heart pacer in accordance with claim 36 further including means under external control for setting said predetermined atrial upper rate.

55. A heart pacer in accordance with claim 36 wherein said controlling means causes the time intervals between successive pacing pulses generated by said ventricular pulse generating means in increase in equal increments as its rate of operation decreases.

56. A heart pacer in accordance with claim 55 further including means for generating atrial pacing pulses, and means for controlling an atrial pacing pulse to be generated approximately simultaneously with each generated ventricular pacing pulse during the time that the operating rate of said ventricular pulse generating means decreases.

57. A heart pacer in accordance with claim 56 further including means for inhibiting operation of said atrial pulse generating means while said ventricular pulse generating means operates at said constant rate.

58. A heart pacer in accordance with claim 36 further including means for preventing the operation of said ventricular pulse generating means to be synchronized to the sensing of atrial beats when said atrial rate falls below a predetermined minimum value.

59. A heart pacer in accordance with claim 36 further including means for sensing ventricular beats, means for generating atrial pacing pulses, means for synchronizing the operation of said atrial pulse generating means to the operation of said ventricular beat sensing means, and means for inhibiting operation of said atrial pulse generating means when said ventricular pulse generating means operates at said constant rate.

60. A heart pacer in accordance with claim 59 wherein said atrial pulse generating means operates approximately simultaneously with said ventricular pulse generating means during the time that the operating rate of the latter is caused to decrease.

61. A heart pacer in accordance with claim 36 wherein, following operation of said ventricular pulse generating means at said constant rate, said controlling means causes operation at said constant rate to persist until said atrial rate falls below said predetermined atrial upper rate at which time said ventricular pulse generating means once again operates in synchronism with said atrial beat sensing means.

62. A heart pacer in accordance with claim 36 wherein said controlling means, in controlling said ventricular pulse generating means to operate in synchronism with said atrial beat sensing means, ignores the sensing of any atrial beat which occurs during a refractory period which follows an operation of said ventricular pulse generating means.

63. A heart pacer in accordance with claim 62 wherein said atrial rate determining means includes in its determination of atrial rate an atrial beat which is sensed during said refractory period.

64. A heart pacer in accordance with claim 63 further including means for sensing ventricular beats, and means for preventing said atrial rate determining means from including in its determination of atrial rate any sensed atrial beat which precedes a sensed ventricular beat by less than a predetermined interval.

65. A heart pacer in accordance with claim 36 further including means for generating atrial pacing pulses, means for sensing ventricular beats, and means for controlling an atrial pacing pulse to be generated approximately simultaneously with each sensed ventricular beat during the time that the operating rate of said ventricular pulse generating means decreases.

66. A heart pacer in accordance with claim 65 further including means for inhibiting operation of said atrial pulse generating means while said ventricular pulse generating means operates at said constant rate.

67. A heart pacer comprising means for sensing atrial beats; means for generating ventricular pacing pulses; means responsive to said atrial beat sensing means for determining the atrial rate; and means for controlling said ventricular pulse generating means to operate in synchronism with said atrial beat sensing means when said atrial rate is below a predetermined atrial upper rate, and for controlling the operating rate of said ventricular pulse generating means to decrease over at least several cycles of operation to a constant rate independent of said atrial beat sensing means when said atrial rate rises above said predetermined atrial upper rate.

68. A heart pacer in accordance with claim 67 wherein said controlling means causes the ratio of the number of sensed atrial beats to the number of generated ventricular pacing pulses to equal N:(N−1), with N decreasing as the rate at which atrial beats are sensed increases, while said atrial rate is still below but is in the vicinity of said predetermined atrial upper rate; and said controlling means causes the operating rate of said ventricular pulse generating means to start decreasing independent of said atrial beat sensing means before said ratio has reach 2:1.

69. A heart pacer in accordance with claim 68 wherein said controlling means causes the operating rate of said ventricular pulse generating means to start decreasing after said ratio has reached 3:2.

70. A heart pacer in accordance with claim 67 wherein said controlling means limits the minimum operating rate of said ventricular pulse generating means to a standby value, and said constant rate is higher than said standby value.

71. A heart pacer in accordance with claim 67 further including means under external control for setting the initial rate at which said ventricular pulse generating means first operates when said atrial rate first rises above said predetermined atrial upper rate, the operating rate of said ventricular pulse generating means then decreasing independent of said atrial beat sensing means from said initial rate to said constant rate.

72. A heart pacer in accordance with claim 67 further including means under external control for setting said predetermined atrial upper rate.

73. A heart pacer in accordance with claim 67 wherein said controlling means causes the time intervals between successive pacing pulses generated by said ventricular pulse generating means to increase in equal increments as its rate of operation decreases independent of said atrial beat sensing means.

74. A heart pacer in accordance with claim 67 further including means for generating atrial pacing pulses, and means for controlling an atrial pacing pulse to be generated approximately simultaneously with each generated ventricular pacing pulse during the time that the operating rate of said ventricular pulse generating means decreases independent of said atrial beat sensing means.

75. A heart pacer in accordance with claim 74 further including means for inhibiting operation of said atrial pulse generating means while said ventricular pulse generating means operates at said constant rate.

76. A heart pacer in accordance with claim 67 further including means for preventing the operation of said ventricular pulse generating means to be synchronized to the sensing of atrial beats when said atrial rate falls below a predetermined minimum value.

77. A heart pacer in accordance with claim 67 further including means for sensing ventricular beats, means for generating atrial pacing pulses, means for synchronizing the operation of said atrial pulse generating means to the operation of said ventricular beat sensing means, and means for inhibiting operation of said atrial pulse generating means when said ventricular pulse generating means operates at said constant rate.

78. A heart pacer in accordance with claim 77 wherein said atrial pulse generating means operates approximately simultaneously with said ventricular beat sensing means during the time that the operating rate of said ventricular pulse generating means is caused to decrease independent of said atrial beat sensing means.

79. A heart pacer in accordance with claim 67 wherein, following operation of said ventricular pulse generating means at said constant rate, said controlling means causes operation at said constant rate to persist until said atrial rate falls below said predetermined atrial upper rate at which time said ventricular pulse generating means once again operates in synchronism with said atrial beat sensing means.

80. A heart pacer in accordance with claim 67 wherein said controlling means, in controlling said ventricular pulse generating means to operate in synchronism with said atrial beat sensing means, ignores the sensing of any atrial beat which occurs during a refractory period which follows an operation of said ventricular pulse generating means.

81. A heart pacer in accordance with claim 80 wherein said atrial rate determining means includes in its determination of atrial rate an atrial beat which is sensed during said refractory period.

82. A heart pacer in accordance with claim 81 further including means for sensing ventricular beats, and means for preventing said trial rate determining means from including in its determination of atrial rate any sensed atrial beat which precedes a sensed ventricular beat by less than a predetermined interval.

83. A heart pacer comprising means for sensing atrial beats; means for generating ventricular pacing pulses; means responsive to said atrial beat sensing means for determining the atrial rate as a function of the number of atrial beats which occur during a measurement interval which is sufficiently long to allow an average value to be determined; means for controlling the mode in which said ventricular pulse generating means operates relative to the operation of said atrial beat sensing means dependent upon whether said atrial rate is above or below an atrial upper rate; said ventricular pulse generating means having its operation synchronized to that of said atrial beat sensing means in at least one mode in which the sensing of any atrial beat which occurs during a refractory period which follows an operation of said ventricular pulse generating means is ignored; said atrial rate determining means including in its determination of atrial rate an atrial beat which is sensed during said refractory period; means for sensing ventricular beats; and means for preventing said atrial rate determining means from including in its determination of atrial rate any sensed atrial beat which precedes a sensed ventricular beat by less than a predetermined interval.

84. A heart pacer in accordance with claim 83 wherein said ventricular pulse generating means operates in synchronism with said atrial beat sensing means when said atrial rate is below said atrial upper rate, and operates at a constant rate independent of said atrial beat sensing means when said atrial rate is above said atrial upper rate.

85. A heart pacer in accordance with claim 84 wherein the operating rate of said ventricular pulse generating means decreases gradually toward said constant rate following said atrial rate first rising above said atrial upper rate.

86. A heart pacer in accordance with claim 85 wherein the ratio of the number of sensed atrial beats to the number of generated ventricular pacing pulses is equal to N:(N−1), with N decreasing as the rate at which atrial beats are sensed increases, while said atrial rate is still below but is in the vicinity of said atrial upper rate; and the operating rate of said ventricular pulse generating means starts reducing gradually before said ratio has reached 2:1.

87. A heart pacer in accordance with claim 86 wherein the operating rate of said ventricular pulse generating means starts reducing gradually after said ratio has reached 3:2.

88. A heart pacer in accordance with claim 85 further including means under external control for setting the initial rate at which said ventricular pulse generating means first operates when said atrial rate first rises above said atrial upper rate, the operating rate of said ventricular pulse generating means then decreasing gradually from said initial rate to said constant rate.

89. A heart pacer in accordance with claim 88 wherein said initial rate is settable to a value higher than that at which said ventricular pulse generating means operates when said atrial rate first rises above said predetermined atrial upper rate.

90. A heart pacer in accordance with claim 85 further including means under external control for setting said atrial upper rate.

91. A heart pacer in accordance with claim 85 wherein the time intervals between successive pacing pulses generated by said ventricular pulse generating means increase in equal increments as its rate of operation decreases gradually.

92. A heart pacer in accordance with claim 85 further including means for generating atrial pacing pulses, and means for controlling an atrial pacing pulse to be generated approximately simultaneously with each generated ventricular pacing pulse during the time that the operating rate of said ventricular pulse generating means decreases gradually.

93. A heart pacer in accordance with claim 92 further including means for inhibiting operation of said atrial pulse generating means while said ventricular pulse generating means operates at said constant rate.

94. A heart pacer in accordance with claim 85 further including means for preventing the operation of said ventricular pulse generating means to be synchronized to the sensing of atrial beats when said atrial rate falls below a predetermined minimum value.

95. A heart pacer in accordance with claim 85 further including means for sensing ventricular beats, means for generating atrial pacing pulses, means for synchronizing the operation of said atrial pulse generating means to the operation of said ventricular beat sensing means, and means for inhibiting operation of said atrial pulse generating means when said ventricular pulse generating means operates at said constant rate.

96. A heart pacer in accordance with claim 95 wherein said atrial pulse generating means operates approximately simultaneously with said ventricular pulse generating means during the time that the operating rate of the latter decreases gradually.

97. A heart pacer in accordance with claim 85 wherein, following operation of said ventricular pulse generating means at said constant rate, operation at said constant rate persists until said atrial rate falls below said atrial upper rate at which time said ventricular pulse generating means once again operates in synchronism with said atrial beat sensing means.

98. A heart pacer in accordance with claim 85 further including means for sensing ventricular beats, means for generating atrial pacing pulses, means for synchronizing the operation of said atrial pulse generating means to the operation of said ventricular beat sensing means, and means for selectively disabling operation of said atrial pulse generating means as the operating rate of said ventricular pulse generating means decreases gradually.

99. A heart pacer in accordance with claim 98 further including means for selectively inhibiting the generation of ventricular pacing pulses as the operating rate of said ventricular pulse generating means decreases gradually.

100. A heart pacer in accordance with claim 85 further including means for selectively inhibiting the generation of ventricular pacing pulses as the operating rate of said ventricular pulse generating means decreases gradually.

101. A heart pacer comprising means for sensing atrial beats; means for generating ventricular pacing pulses; means responsive to said atrial beat sensing means for determining the atrial rate as a function of the number of atrial beats which occur during a measurement interval which is sufficiently long to allow an average value to be determined as opposed to an atrial rate which is a function of only the single interval between two successive atrial beats; and means for controlling the mode in which said ventricular pulse generating means operates relative to the operation of said atrial beat sensing means dependent upon whether said atrial rate is above or below an atrial upper rate; said ventricular pulse generating means having its operation synchronized to that of said atrial beat sensing means in at least one mode in which the sensing of any atrial beat which occurs during a refractory period which follows an operation of said ventricular pulse generating means is ignored; said atrial rate determining means including in its determination of atrial rate an atrial beat which is sensed during said refractory period.

102. A heart pacer in accordance with claim 101 further including means for sensing ventricular beats; and means for preventing said atrial rate determining means from including in its determination of atrial rate any sensed atrial beat which precedes a sensed ventricular beat by less than a predetermined interval.

103. A heart pacer in accordance with claim 101 wherein said ventricular pulse generating means operates in synchronism with said atrial beat sensing means when said atrial rate is below said atrial upper rate, and operates at a constant rate independent of said atrial beat sensing means when said atrial rate is above said atrial upper rate.

104. A heart pacer in accordance with claim 103 wherein the operating rate of said ventricular pulse generating means is decreased to said constant rate over at least several seconds following said atrial rate first rising above said atrial upper rate.

105. A heart pacer in accordance with claim 104 wherein the ratio of the number of sensed atrial beats to the number of generated ventricular pacing pulses is equal to N:(N−1), with N decreasing as the rate at which atrial beats are sensed increases, while said atrial rate is still below but is in the vicinity of said atrial upper rate; and the operating rate of said ventricular pulse generating means starts decreasing before said ratio has reached 2:1.

106. A heart pacer in accordance with claim 105 wherein the operating rate of said ventricular pulse generating means starts decreasing after said ratio has reached 3:2.

107. A heart pacer in accordance with claim 104 further including means for sensing ventricular beats, means for generating atrial pacing pulses, means for synchronizing the operation of said atrial pulse generating means to the operation of said ventricular beat sensing means, and means for selectively disabling operation of said atrial pulse generating means as the operating rate of said ventricular pulse generating means decreases over said at least several seconds.

108. A heart pacer in accordance with claim 107 further including means for selectively inhibiting the generation of ventricular pacing pulses as the operating rate of said ventricular pulse generating means decreases over said at least several seconds.

109. A heart pacer in accordance with claim 104 further including means for selectively inhibiting the generation of ventricular pacing pulses as the operating rate of said ventricular pulse generating means decreases gradually.

110. A heart pacer in accordance with claim 104 further including means under external control for setting the initial rate at which said ventricular pulse generating means first operates when said atrial rate first rises above said atrial upper rate, the operating rate of said ventricular pulse generating means then decreasing over said at least several seconds from said initial rate to said constant rate.

111. A heart pacer in accordance with claim 110 wherein said initial rate is settable to a value higher than that at which said ventricular pulse generating means operates when said atrial rate first rises above said predetermined atrial upper rate.

112. A heart pacer in accordance with claim 104 further including means under external control for setting said atrial upper rate.

113. A heart pacer in accordance with claim 104 wherein the rate of operation of said ventricular pulse generating means decreases at a constant rate over said at least several seconds.

114. A heart pacer in accordance with claim 104 further including means for generating atrial pacing pulses, and means for controlling an atrial pacing pulse to be generated approximately simultaneously with each generated ventricular pacing pulse during the time that the operating rate of said ventricular pulse generating means decreases over said at least several seconds.

115. A heart pacer in accordance with claim 114 further including means for inhibiting operation of said atrial pulse generating means while said ventricular pulse generating means operates at said constant rate.

116. A heart pacer in accordance with claim 104 further including means for preventing the operation of said ventricular pulse generating means to be synchronized to the sensing of atrial beats when said atrial rate falls below a predetermined minimum value.

117. A heart pacer in accordance with claim 104 further including means for sensing ventricular beats, means for generating atrial pacing pulses, means for synchronizing the operation of said atrial pulse generating means to the operation of said ventricular beat sensing means, and means for inhibiting operation of said atrial pulse generating means when said ventricular pulse generating means operates at said constant rate.

118. A heart pacer in accordance with claim 117 wherein said atrial pulse generating means operates approximately simultaneously with said ventricular pulse generating means during the time that the operating rate of the latter decreases over said at least several seconds.

119. A heart pacer in accordance with claim 104 wherein, following operation of said ventricular pulse generating means at said constant rate, operation at said constant rate persists until said atrial rate falls below said atrial upper rate at which time said ventricular pulse generating means once again operates in synchronism with said atrial beat sensing means.

* * * * *